United States Patent [19]
Laux et al.

[11] Patent Number: 5,827,259
[45] Date of Patent: *Oct. 27, 1998

[54] ABSORBENT ARTICLE WITH WAIST ELASTIC AND CONTAINMENT SYSTEM

[75] Inventors: Daniel Richard Laux; Lynn Carol Brud, both of Appleton; Barbara Ann Gossen, Oshkosh; Eric Donald Johnson, Larsen; Cynthia Helen Nordness, Oshkosh; Deborah Lynn Proxmire, Larsen; Mark Louis Robinson, Appleton; Paula Mary Sosalla, Appleton; Robert Alan Stevens, Appleton, all of Wis.

[73] Assignee: Kimberly-Clark Worldwide, Inc., Neenah, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 560,524

[22] Filed: Dec. 18, 1995

Related U.S. Application Data

[60] Provisional application No. 60/007,889 Oct. 25, 1995 and provisional application No. 60/007,912 Dec. 4, 1995.

[51] Int. Cl.⁶ .................................................. A61F 13/15
[52] U.S. Cl. ..................................... 604/385.2; 604/385.1
[58] Field of Search ............................. 604/385.1, 385.2, 604/386, 378, 381, 382, 387, 373

[56] References Cited

U.S. PATENT DOCUMENTS

| | | | |
|---|---|---|---|
| H1630 | 1/1997 | Roe et al. | 604/385.2 |
| 2,532,029 | 11/1950 | Medoff. | |
| 2,545,674 | 3/1951 | Ralph. | |
| 2,575,163 | 11/1951 | Donovan. | |

(List continued on next page.)

FOREIGN PATENT DOCUMENTS

| | | |
|---|---|---|
| 2122700 A1 | 5/1994 | Canada. |
| 2130245 A1 | 8/1994 | Canada. |
| 2130318 A1 | 8/1994 | Canada. |

(List continued on next page.)

OTHER PUBLICATIONS

Federal Test Method Standard (FTMS) No. 191, Method 5514, "Water Resistance of Cloth; Low Range, Hydrostatic Pressure Method," Jul. 20, 1978.
TAPPI Official Test Method T 543 om–94, "Bending Resistance of Paper (Gurley Type Tester)," published by the TAPPI Press, Atlanta, Georgia, pp. 1–5.
Derwent World Patent Database abstract of FR 2,680,316: Description of B. Deleu et al., "Disposable Nappy".

*Primary Examiner*—Mark O. Polutta
*Attorney, Agent, or Firm*—Paul Yee

[57] ABSTRACT

An absorbent article includes a longitudinal length dimension, a lateral cross-dimension, a front waistband portion, a back waistband portion, an intermediate portion which interconnects the front and back waistband portions, and a pair of laterally opposed elasticized side margins. The article has a backsheet layer, and a liquid permeable topsheet layer connected in superposed relation to the backsheet layer. An absorbent body is sandwiched between the topsheet layer and the backsheet layer, and an elasticized, waist pocket member is connected to at least one of the backsheet and topsheet layers along at least one end margin of the article. The waist pocket member includes an extending flange section and an extending pocket section. The pocket section of the waist pocket member includes a substantially fixed edge portion secured to the article, and an elasticized, gathered moveable edge portion, which is longitudinally spaced from the fixed edge portion. The pocket section can also include a substantially liquid impermeable pocket barrier layer, and a pocket fabric layer connected in facing relation with the pocket barrier layer. Additionally, a plurality of separate, laterally extending pocket elastic members can be sandwiched between the pocket barrier layer and the pocket fabric layer to thereby provide an elasticized waist pocket composite which is substantially laterally gathered.

24 Claims, 5 Drawing Sheets

U.S. PATENT DOCUMENTS

| | | |
|---|---|---|
| 2,575,164 | 11/1951 | Donovan . |
| 2,893,393 | 7/1959 | Pressley . |
| 2,956,564 | 10/1960 | Ohara . |
| 3,386,442 | 6/1968 | Sabee . |
| 3,901,236 | 8/1975 | Assarsson et al. . |
| 4,076,663 | 2/1978 | Masuda et al. . |
| 4,286,082 | 8/1981 | Tsubakimoto et al. . |
| 4,381,781 | 5/1983 | Sciaraffa et al. .................... 604/372 |
| 4,585,448 | 4/1986 | Enloe ................................. 604/378 |
| 4,636,207 | 1/1987 | Buell ................................. 604/370 |
| 4,643,728 | 2/1987 | Karami ............................. 604/385 A |
| 4,657,539 | 4/1987 | Lasse . |
| 4,662,877 | 5/1987 | Williams . |
| 4,663,220 | 5/1987 | Wisneski et al. ................... 428/221 |
| 4,681,579 | 7/1987 | Toussant et al. ................. 604/385 R |
| 4,695,278 | 9/1987 | Lawson . |
| 4,699,823 | 10/1987 | Kellenberger et al. .............. 428/219 |
| 4,704,116 | 11/1987 | Enloe ............................. 604/385 A |
| 4,738,677 | 4/1988 | Foreman . |
| 4,743,246 | 5/1988 | Lawson ........................... 604/385 A |
| 4,753,646 | 6/1988 | Enloe ............................. 604/385 R |
| 4,770,656 | 9/1988 | Proxmire et al. .................... 604/393 |
| 4,795,454 | 1/1989 | Dragoo .............................. 604/385.2 |
| 4,808,177 | 2/1989 | DesMarais et al. ................. 604/385.1 |
| 4,816,025 | 3/1989 | Foreman ........................... 604/385.2 |
| 4,822,435 | 4/1989 | Igaue et al. ......................... 156/164 |
| 4,834,740 | 5/1989 | Suzuki et al. ..................... 604/385.2 |
| 4,846,823 | 7/1989 | Enloe ............................... 604/385.2 |
| 4,846,825 | 7/1989 | Enloe et al. ...................... 604/385.1 |
| 4,861,652 | 8/1989 | Lippert et al. ....................... 428/284 |
| 4,883,480 | 11/1989 | Huffman et al. .................... 604/385.1 |
| 4,892,528 | 1/1990 | Suzuki et al. ..................... 604/385.2 |
| 4,904,251 | 2/1990 | Igaue et al. ....................... 604/385.2 |
| 4,916,005 | 4/1990 | Lippert et al. ....................... 428/192 |
| 4,938,754 | 7/1990 | Mesek .............................. 604/385.2 |
| 4,938,755 | 7/1990 | Foreman ........................... 604/385.2 |
| 4,949,668 | 8/1990 | Heindel et al. ..................... 118/314 |
| 4,998,929 | 3/1991 | Björksund et al. ................. 604/385.2 |
| 5,019,066 | 5/1991 | Freeland et al. ................... 604/385.2 |
| 5,021,051 | 6/1991 | Hiuke ............................... 604/385.2 |
| 5,026,364 | 6/1991 | Robertson ......................... 604/385.1 |
| 5,028,224 | 7/1991 | Pieper et al. ........................ 425/80.1 |
| 5,032,120 | 7/1991 | Freeland et al. ................... 604/385.2 |
| 5,061,261 | 10/1991 | Suzuki et al. ..................... 604/385.2 |
| 5,064,489 | 11/1991 | Ujimoto et al. ...................... 156/164 |
| 5,080,658 | 1/1992 | Igaue et al. ....................... 604/385.2 |
| 5,085,654 | 2/1992 | Buell ................................. 604/370 |
| 5,087,255 | 2/1992 | Sims ................................ 604/385.1 |
| 5,114,420 | 5/1992 | Igaue et al. ....................... 604/385.2 |
| 5,137,526 | 8/1992 | Coates .............................. 604/391 |
| 5,147,343 | 9/1992 | Kellenberger ....................... 604/368 |
| 5,167,653 | 12/1992 | Igaue et al. ....................... 604/385.2 |
| 5,176,672 | 1/1993 | Bruemmer et al. ................. 604/385.1 |
| 5,188,627 | 2/1993 | Igaue et al. ....................... 604/385.2 |
| 5,221,277 | 6/1993 | Beplate ............................. 604/394 |
| 5,226,992 | 7/1993 | Morman ............................. 156/62.4 |
| 5,246,432 | 9/1993 | Suzuki et al. ..................... 604/385.2 |
| 5,275,590 | 1/1994 | Huffman et al. .................... 604/385.2 |
| 5,292,316 | 3/1994 | Suzuki .............................. 604/385.2 |
| 5,304,159 | 4/1994 | Tanji et al. ........................ 604/385.2 |
| 5,304,160 | 4/1994 | Igaue et al. ....................... 604/385.2 |
| 5,308,344 | 5/1994 | Toth ................................. 604/378 |
| 5,330,598 | 7/1994 | Erdman et al. ...................... 156/164 |
| 5,340,648 | 8/1994 | Rollins et al. ....................... 428/343 |
| 5,342,342 | 8/1994 | Kitaoka ............................. 604/385.2 |
| 5,344,516 | 9/1994 | Tanji et al. ......................... 156/164 |
| 5,360,422 | 11/1994 | Brownlee et al. .................. 604/385.2 |
| 5,368,584 | 11/1994 | Clear et al. ....................... 604/385.2 |
| 5,397,318 | 3/1995 | Dreier .............................. 604/385.2 |
| 5,399,219 | 3/1995 | Roessler et al. ..................... 156/259 |
| 5,407,438 | 4/1995 | Hedlund et al. .................... 604/385.2 |
| 5,409,476 | 4/1995 | Coates .............................. 604/391 |
| 5,417,680 | 5/1995 | Kimura et al. ..................... 604/385.2 |
| 5,451,219 | 9/1995 | Suzuki et al. ..................... 604/385.2 |
| 5,454,803 | 10/1995 | Sageser et al. ..................... 604/385.2 |
| 5,476,458 | 12/1995 | Glaug et al. ......................... 604/378 |
| 5,486,166 | 1/1996 | Bishop et al. ....................... 604/366 |
| 5,489,282 | 2/1996 | Zehner et al. ..................... 604/385.1 |
| 5,490,846 | 2/1996 | Ellis et al. ........................... 604/386 |
| 5,501,756 | 3/1996 | Rollins et al. ....................... 156/167 |
| 5,507,909 | 4/1996 | Rollins et al. ....................... 156/425 |
| 5,527,300 | 6/1996 | Sauer ................................ 604/378 |
| 5,527,302 | 6/1996 | Endres et al. ...................... 604/385.1 |
| 5,531,730 | 7/1996 | Dreier .............................. 604/385.2 |
| 5,540,671 | 7/1996 | Dreier .............................. 604/385.2 |
| 5,540,672 | 7/1996 | Roessler et al. .................... 604/385.2 |
| 5,540,796 | 7/1996 | Fries ................................ 156/164 |
| 5,542,943 | 8/1996 | Sageser ............................. 604/385.2 |
| 5,554,142 | 9/1996 | Dreier et al. ...................... 604/385.1 |
| 5,558,660 | 9/1996 | Dreier .............................. 604/385.2 |
| 5,558,661 | 9/1996 | Roe et al. .......................... 604/385.2 |
| 5,562,650 | 10/1996 | Everett et al. ...................... 604/385.2 |
| 5,565,050 | 10/1996 | Sageser et al. ....................... 156/73.1 |
| 5,567,254 | 10/1996 | Sageser .............................. 156/73.1 |
| 5,569,227 | 10/1996 | Vandemoortele et al. ........... 604/385.2 |
| 5,571,096 | 11/1996 | Dobrin et al. ....................... 604/383 |
| 5,575,785 | 11/1996 | Gryskiewicz et al. ............... 604/385.2 |
| 5,576,091 | 11/1996 | Zajaczkowski et al. .............. 428/192 |
| 5,577,540 | 11/1996 | Sageser ............................. 156/226 |
| 5,582,606 | 12/1996 | Bruemmer et al. ................. 604/385.2 |
| 5,584,828 | 12/1996 | Yamamoto et al. ................. 604/385.2 |
| 5,593,401 | 1/1997 | Sosalla et al. ...................... 604/385.2 |
| 5,595,618 | 1/1997 | Fries et al. ......................... 156/164 |
| 5,599,338 | 2/1997 | Enloe ............................... 604/385.2 |
| 5,599,417 | 2/1997 | Glaug et al. ......................... 156/227 |
| 5,601,543 | 2/1997 | Dreier et al. ...................... 604/385.1 |
| 5,601,544 | 2/1997 | Glaug et al. ....................... 604/385.2 |
| 5,601,546 | 2/1997 | Tanji et al. ........................ 604/385.2 |
| 5,605,735 | 2/1997 | Zehner et al. ....................... 428/100 |
| 5,624,426 | 4/1997 | Roe et al. .......................... 601/385.2 |
| 5,628,737 | 5/1997 | Dobrin et al. ....................... 604/383 |

FOREIGN PATENT DOCUMENTS

| | | |
|---|---|---|
| 2138428 A1 | 12/1994 | Canada . |
| 0217032 A3 | 4/1987 | European Pat. Off. . |
| 0243013 A1 | 10/1987 | European Pat. Off. . |
| 0312071 A2 | 4/1989 | European Pat. Off. . |
| 0339461 B1 | 11/1989 | European Pat. Off. . |
| 0376022 B1 | 7/1990 | European Pat. Off. . |
| 0386815 A2 | 9/1990 | European Pat. Off. . |
| 0403832 B1 | 12/1990 | European Pat. Off. . |
| 0404648 B1 | 12/1990 | European Pat. Off. . |
| 0433951 A2 | 6/1991 | European Pat. Off. . |
| 0 532 035 A3 | 3/1993 | European Pat. Off. . |
| 0329160 B1 | 9/1993 | European Pat. Off. . |
| 0 568 085 A1 | 11/1993 | European Pat. Off. . |
| 0 622 063 A3 | 11/1994 | European Pat. Off. . |
| 0 664 997 A1 | 8/1995 | European Pat. Off. . |
| 0 678 289 A1 | 10/1995 | European Pat. Off. . |
| 0 678 290 A1 | 10/1995 | European Pat. Off. . |
| 0 745 367 A2 | 12/1996 | European Pat. Off. . |
| 0 750 894 A2 | 1/1997 | European Pat. Off. . |
| 0 750 895 A2 | 1/1997 | European Pat. Off. . |
| 2677541 A1 | 12/1992 | France . |
| H7-184954 | 7/1995 | Japan . |
| H7-184955 | 7/1995 | Japan . |
| 92/4165 | 6/1992 | South Africa . |
| 2159693 | 12/1985 | United Kingdom . |
| 2 216 393 | 10/1989 | United Kingdom . |
| 2216393 | 10/1989 | United Kingdom . |
| 2262873 | 7/1993 | United Kingdom . |
| 2265550 | 10/1993 | United Kingdom . |

| | | | | | |
|---|---|---|---|---|---|
| 2265834 | 10/1993 | United Kingdom . | WO 94/10951 | | |
| 2266055 | 10/1993 | United Kingdom . | A1 | 5/1994 | WIPO . |
| 2266225 | 10/1993 | United Kingdom . | WO 94/14395 | | |
| 2266444 | 11/1993 | United Kingdom . | A1 | 7/1994 | WIPO . |
| 2268389 | 1/1994 | United Kingdom . | 9418927 | 9/1994 | WIPO . |
| 2270247 | 3/1994 | United Kingdom . | WO 94/18927 | | |
| 2 271 501 | 4/1994 | United Kingdom . | A1 | 9/1994 | WIPO . |
| 2275610 | 9/1994 | United Kingdom . | WO 94/28840 | | |
| 2275611 | 9/1994 | United Kingdom . | A2 | 12/1994 | WIPO . |
| 2278993 | 12/1994 | United Kingdom . | 9514453 | 6/1995 | WIPO . |
| 2280374 | 2/1995 | United Kingdom . | 9522951 | 8/1995 | WIPO . |
| 2 284 538 | 6/1995 | United Kingdom . | WO 95/25493 | | |
| 2285409 | 7/1995 | United Kingdom . | A1 | 9/1995 | WIPO . |
| 9108717 | 6/1991 | WIPO . | WO 95/25494 | | |
| 9207533 | 5/1992 | WIPO . | A1 | 9/1995 | WIPO . |
| 9209253 | 6/1992 | WIPO . | WO 95/32699 | | |
| 9212648 | 8/1992 | WIPO . | A1 | 12/1995 | WIPO . |
| 9222271 | 12/1992 | WIPO . | WO 96/05792 | | |
| 9303698 | 3/1993 | WIPO . | A1 | 2/1996 | WIPO . |
| 9305742 | 4/1993 | WIPO . | WO 96/09025 | | |
| WO 93/05744 | | | A1 | 3/1996 | WIPO . |
| A1 | 4/1993 | WIPO . | WO 96/24320 | | |
| 9312746 | 7/1993 | WIPO . | A1 | 8/1996 | WIPO . |
| 9323000 | 11/1993 | WIPO . | WO 96/31176 | 10/1996 | WIPO . |

ABSORBENT ARTICLE WITH WAIST ELASTIC AND CONTAINMENT SYSTEM

This application has the benefit of provisional application 60/007,889 filed Oct. 25, 1995, now abandoned, and the benefit of provisional application 60/007,912 entitled "AN ABSORBENT ARTICLE WITH IMPROVED ELASTIC MARGINS AND CONTAINMENT SYSTEM" filed Dec. 4, 1995, now abandoned.

FIELD OF THE INVENTION

The present invention relates to an article having one or more elasticized, peripheral margins. More particularly, the invention relates to an article which incorporates a distinctively elasticized barrier or containment system at a waistband portion of the article.

BACKGROUND OF THE INVENTION

Conventional absorbent articles, such as disposable diapers, have been constructed with various types of elasticized waistbands and elasticized leg bands or leg cuffs. Such articles have also included additional, elasticized containment or barrier flaps at the leg and/or waist sections of the article. Particular article designs have incorporated a stretchable outer cover composed of an elastomeric web material, such as a stretch-bonded laminate which includes a layer of nonwoven fabric. Other conventional designs have included separate elastomeric or nonelastomeric side panel members connected to the lateral side edges of a backsheet or outercover member, and have included fastening systems and fastening tabs connected to the side panels for securing the article on a wearer.

Articles which incorporate conventional waist flap configurations, however, have exhibited various shortcomings. For example, it has been difficult to maintain the desired operation of the waist flaps when the articles are being worn. Even when the waist flaps are constructed of an elastomeric material or otherwise elasticized, it has been difficult to maintain contact between the movable edge of the waist flap and the wearers body and has been difficult to reliably hold the flap open for an effective receipt and containment of urine and feces. As a result, there has been a continued need for improved containment structures at the leg and waist regions of the absorbent articles.

BRIEF DESCRIPTION OF THE INVENTION

The present invention can provide a distinctive article which includes a longitudinal length dimension, a lateral cross-dimension, a front waistband portion, a back waistband portion, an intermediate portion which interconnects the front and back waistband portions, and a pair of laterally opposed elasticized side margins. The article has a backsheet layer, and a liquid permeable topsheet layer connected in superposed relation to the backsheet layer. An absorbent body is sandwiched between the topsheet layer and the backsheet layer, and an elasticized, waist pocket member is connected to at least one of the backsheet and topsheet layers along at least one end margin of the article. The waist pocket member includes an extending flange section and an extending pocket section. The pocket section of the waist pocket member includes a substantially fixed edge portion secured to the article, and an elasticized, gathered moveable edge portion, which is longitudinally spaced from the fixed edge portion. In particular aspects, the pocket section can also include a substantially liquid impermeable pocket barrier layer, and a pocket fabric layer connected in facing relation with the pocket barrier layer. In other aspects, a plurality of separate, laterally extending pocket elastic members can be sandwiched between the pocket barrier layer and the pocket fabric layer to provide an elasticized waist pocket composite which is substantially laterally gathered.

The various aspects of the invention can provide a barrier flap structure which can more reliably and more effectively maintain an open position when the associated absorbent article is being worn. In addition, the open flap configuration can be sustained while avoiding excessive irritation of the wearers skin. The arrangements of the constituent components and the combination of operational parameters, such as the controlled stiffness and the controlled articulation of the barrier flap, can advantageously provide an improved absorbent structure which can have less leakage, and can afford increased comfort to the wearer.

BRIEF DESCRIPTION OF THE DRAWINGS

The invention will be more fully understood and further advantages will become apparent when reference is made to the following detailed description and accompanying drawings in which.

DETAILED DESCRIPTION OF THE INVENTION

The present invention will be described herein in relationship to producing an elasticized containment system for absorbent articles, particularly disposable absorbent articles. The articles can be placed against or in proximity to the body of a wearer to absorb and contain various exudates discharged from the body, and are intended to be discarded after a limited period of use. The articles are not intended to be laundered or otherwise restored for re-use. While the present description will particularly be made in the context of a diaper article, it should be understood that the present invention is also applicable to other articles, such as caps, gowns, drapes, covers, adult incontinence garments, sanitary napkins, children's training pants, and the like.

In addition, the invention will be described in the context of its various configurations and aspects. It should be appreciated that alternative arrangements of the invention can comprise any combination which includes one or more of the various configurations and aspects of the invention.

Figure 1:
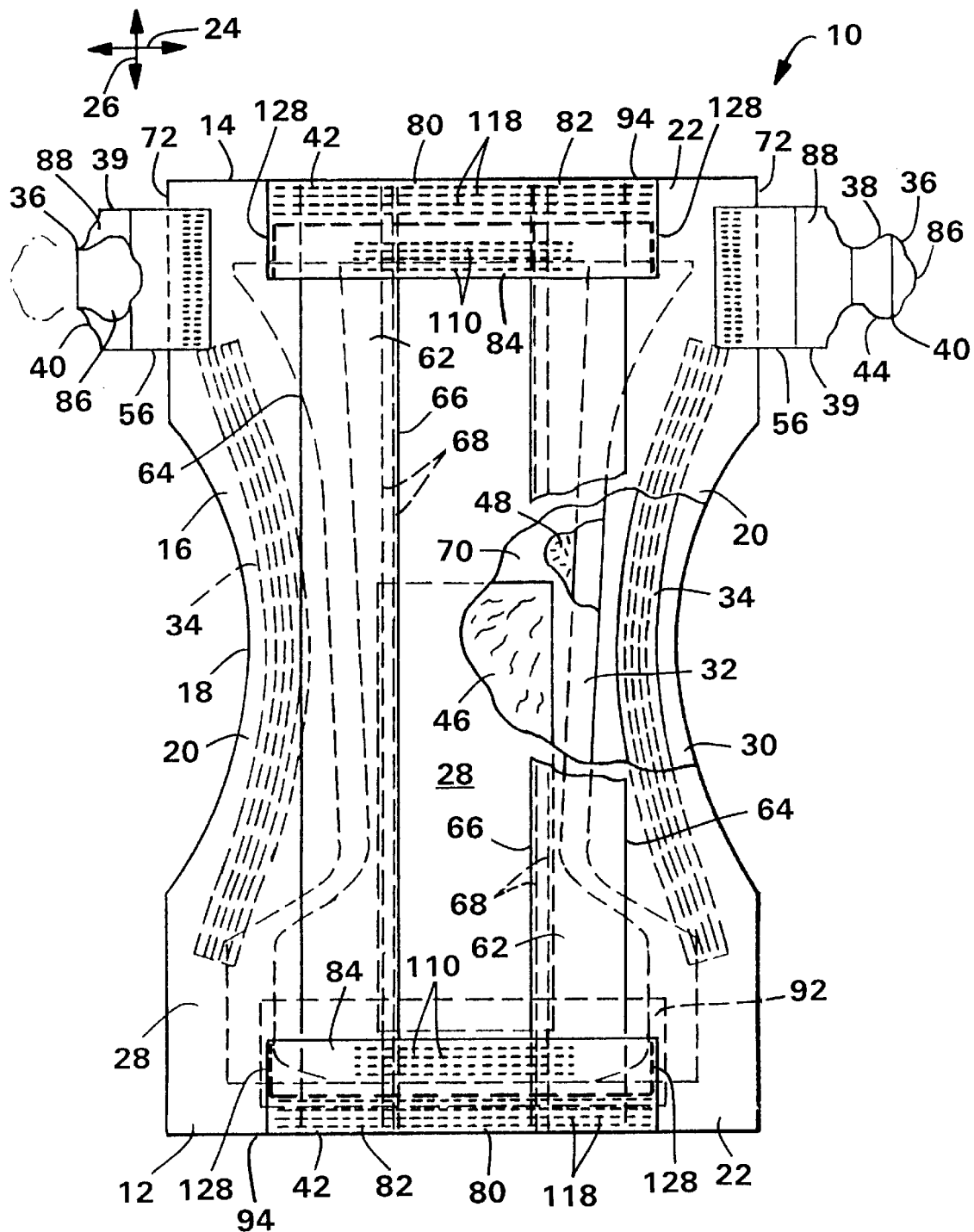
FIG. 1 representatively shows a partially cut-away, top view of an article of the invention.
Figure 2:
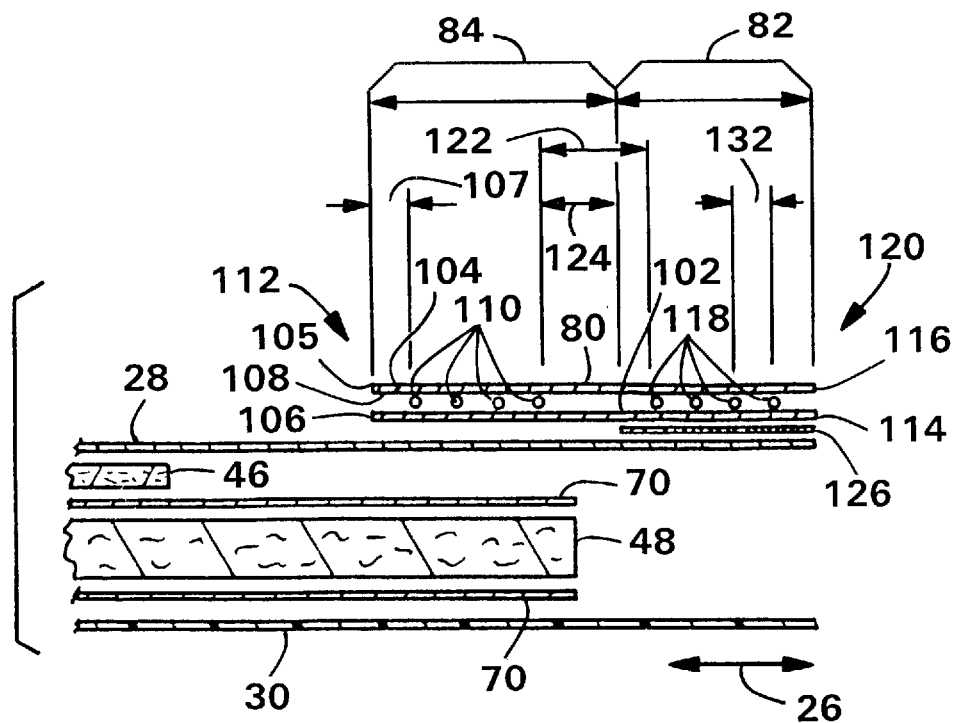
FIG. 2 representatively shows an schematic, expanded cross-sectional view of the waist elastic system and the waist, barrier flap system of the invention taken along a longitudinal centerline of the article when the flap or pocket section is in its flat-out, uncontracted condition.
Figure 3:
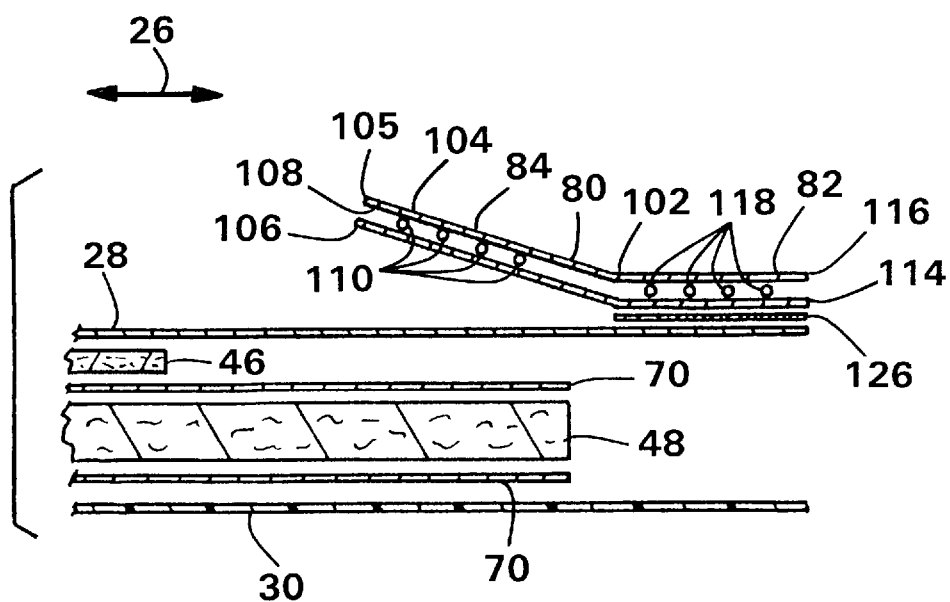
FIG. 3 representatively shows an schematic, expanded cross-sectional view of the waist elastic system and the waist, barrier flap system of the invention taken when the flap or pocket section is in its contracted and opened condition.

With reference to FIGS. 1, 2 and 3, a representative article, such as a diaper 10, includes a longitudinal length dimension 26, a lateral cross-dimension 24, a front waistband portion 12, a back waistband portion 14, an intermediate portion 16 which interconnects the front and back waistband portions, and a pair of laterally opposed elasticized side margins 20. The article has a backsheet layer 30, and a liquid permeable topsheet layer 28 connected in superposed relation to the backsheet layer. An absorbent body 32 is sandwiched between the topsheet layer and the backsheet layer, and an elasticized, waist pocket member 80 is connected to at least one of the backsheet and topsheet layers along at least one end margin 22 of the article.

The representatively shown article includes longitudinally opposed end margins 22 and a pair of laterally opposed elasticized side margins 20. The elasticized, waist pocket member 80 is connected to at least one of the backsheet and topsheet layers along at least one end margin 22 of the article. The shown waist pocket member 80 includes an extending flange section 82 and an extending pocket section 84. The pocket section 84 of the waist pocket member 80 includes a substantially fixed edge portion 102 secured to the article, and includes an elasticized, gathered moveable edge portion 104 which is longitudinally spaced from the fixed edge portion 102. The pocket section also includes a substantially liquid impermeable pocket barrier layer 106, and a pocket fabric layer 108 connected in facing relation with the pocket barrier layer. A plurality of separate, laterally extending pocket elastic members 110 are sandwiched between the pocket barrier layer 106 and the pocket fabric layer 108 to provide an elasticized waist pocket composite 112 which is substantially laterally gathered.

A fastening system 40 is connected to the article at either or both of the laterally opposed end regions 72 of at least one of the front and rear waistband sections. A cooperating side panel member 56 can be associated with each fastening system and may be constructed to be nonelasticized, or to be elastically stretchable at least along a laterally extending cross-direction 24 of the article.

FIG. 1 is a representative plan view of diaper 10 of the present invention in its flat-out, uncontracted state (i.e., with all elastic induced gathering and contraction removed). Portions of the structure are partially cut away to more clearly show the interior construction of diaper 10, and the surface of the diaper which contacts the wearer is facing the viewer. The outer edges of the diaper define a periphery in which the longitudinally extending side edge margins are designated 20 and the laterally extending end edge margins are designated 22. The side edges define leg openings for the diaper, and optionally, are curvilinear and contoured. The end edges are shown as straight, but optionally, may be curvilinear.

Diaper 10 typically includes a porous, liquid permeable topsheet 28; a substantially liquid impermeable backsheet 30; an absorbent structure 32, positioned and connected between the topsheet and backsheet; a surge management portion 46; and elastic members, such as leg elastics 34 and waist elastics 42. The surge management portion is positioned in liquid communication with the absorbent structure, and the absorbent structure includes a retention portion 48. The topsheet 28, backsheet 30, absorbent structure 32, surge management portion 46 and the elastic members 34 and 42 may be assembled in a variety of well-known diaper configurations. In addition, the diaper can include a system of legband barrier flaps, such as containment flaps 62.

As representatively shown, the topsheet 28 and backsheet 30 may be generally coextensive, and may have length and width dimensions which are generally larger than the corresponding dimensions of absorbent structure 32. Topsheet 28 is associated with and superimposed on backsheet 30, thereby defining the periphery of diaper 10. The waistband regions comprise those upper portions of diaper 10, which when worn, wholly or partially cover or encircle the waist or mid-lower torso of the wearer. The intermediate, region 16 lies between and interconnects waistband regions 12 and 14, and includes a crotch region 18 which comprises that portion of diaper 10 which, when worn, is positioned between the legs of the wearer and covers the lower torso of the wearer. Thus, the crotch region 18 is an area where repeated fluid surges typically occur in the diaper or other disposable absorbent article.

Topsheet 28 presents a body-facing surface which is compliant, soft-feeling, and nonirritating to the wearer's skin. Further, the topsheet 28 can be less hydrophilic than retention portion 48, and is sufficiently porous to be liquid permeable, permitting liquid to penetrate through its thickness. A suitable topsheet 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Topsheet 28 is typically employed to help isolate the wearer's skin from liquids held in absorbent structure 32. Various woven and nonwoven fabrics can be used for topsheet 28. For example, the topsheet may be composed of a meltblown or spunbonded web of polyolefin fibers. The topsheet may also be a bonded-carded-web composed of natural and/or synthetic fibers.

For the purposes of the present description, the term "nonwoven web" means a web of material which is formed without the aid of a textile weaving or knitting process. The term "fabrics" is used to refer to all of the woven, knitted and nonwoven fibrous webs.

The topsheet fabrics may be composed of a substantially hydrophobic and substantially nonwettable material, and the hydrophobic material may optionally be treated with a surfactant or otherwise processed to impart a desired level of wettability and hydrophilicity. In a particular embodiment of the invention, topsheet 28 can be a nonwoven, spunbond polypropylene fabric composed of about 2.8–3.2 denier fibers formed into a web having a basis weight of about 20 gsm (g/m$^2$) and density of about 0.13 gm/cc. The fabric can be surface treated with a selected amount of surfactant, such as about 0.28% TRITON X-102 surfactant available from Union Carbide, a business having offices in Danbury, Conn. The surfactant can be applied by any conventional means, such as spraying, printing, brush coating or the like.

The surfactant material, such as a conventional wetting agent, can be applied to a medial section of the topsheet layer 28 to provide a greater wettability of the medial section, as compared to a remainder of the topsheet layer 28. In particular configurations, the cross-directional width of the medial section can be substantially equal to or less than the cross-directional width of the surge management portion 46. In alternative configurations, the medial section width can be substantially equal to or less than a cross-directional spacing between a pair of adhesive strips employed to secure the containment flaps 62 onto topsheet 28 and to form a leak resistant barrier seal onto the backsheet 30.

The surfactant-treated medial section can be approximately centered with respect to the longitudinal centerline of the diaper, and can extend along substantially the entire length of the topsheet layer. Alternatively, the surfactant treated medial section can be constructed to extend along only a predetermined portion of the topsheet length.

The various configurations of the invention can include elasticized, legband barrier flaps, such as the illustrated containment flaps 62. The shown configurations, for example, include two containment flaps 62 which are connected to the bodyside surface of topsheet layer 28. Suitable constructions and arrangements for containment flaps 62 are described, for example, in U.S. Pat. 4,704,116 issued Nov. 3, 1987, to K. Enloe, the disclosure of which is hereby incorporated by reference in a manner that is consistent (not contradictory) herewith. Other configurations of the containment flaps 62 are described in U.S. patent application Ser. No. 206,816 of R. Everett et al., filed Mar. 4, 1994 and entitled ABSORBENT ARTICLE HAVING AN IMPROVED SURGE MANAGEMENT (Attorney docket No.11,375), the disclosure of which is hereby incorporated by reference in a manner that is consistent herewith.

Such containment flaps can be attached to topsheet layer 28 along length-wise extending fixed regions, such as fixed edges 64, of the flaps. A movable edge 66 of each containment flap includes a flap elastic member 68 which can comprise one or more individual strands of elastomeric material. For example, a plurality of elastic strands may be configured in a spatially separated, generally parallel arrangement, and a suitable elastic strand can, for example, be composed of a 470 decitex LYCRA elastomer which is available from E. l. DuPont de Nemours, a business having offices in Wilmington, Del. Alternatively, the elastic strands may be composed of 700 denier GLOSPAN S7 spandex elastomer which is available from Globe Manufacturing, a business having offices in Fall River, Mass. Elastic member 68 is connected to the movable edge of the containment flap in an elastically contractible condition such that the contraction of the elastic components thereof gathers and shortens the edge of the containment flap. As a result, the movable edge of each containment flap tends to position itself in a spaced relation away from the bodyside surfaces of topsheet 28 and/or surge management portion 46 toward a generally upright and approximately perpendicular configuration, especially in the crotch section of the diaper. In the shown embodiment, for example, the moveable edge of the containment flap is connected to the flap elastics by partially doubling the flap material back upon itself by a limited amount which is sufficient to enclose the flap elastics 68.

At least a pair of containment, barrier flaps 62 are connected to laterally opposed, longitudinally extending regions of topsheet layer 28, and the connected topsheet regions are located generally adjacent to laterally opposed side edge regions of the medial section of topsheet layer 28. The connected topsheet regions are located substantially laterally inboard of the leg elastics of the diaper article 10, but may optionally be located outboard of the leg elastics.

In the various configurations of the invention, the desired barrier flaps, such as the containment flaps 62 and the waist flaps 84, may, for example, be constructed of a fibrous material which is similar to the material comprising topsheet 28, or similar to the material comprising surge management portion 46. Other conventional materials, such as polymer films, may also be employed. In other aspects of the invention, the barrier flaps are constructed of a material which is permeable only to gas, such as ambient air. Alternative configurations of the invention can include barrier flaps which are constructed of a material which is resistant to a passage of aqueous liquid, such as urine, therethrough. For example, the barrier flaps may be constructed of a spunbond-meltblown-spunbond (SMS) laminate material. In the illustrated embodiment, for example, the barrier flaps can be constructed of a SMS material having a basis weight of about 0.75 osy (about 25 g/m$^2$). The spunbond layers are composed of polypropylene fibers, and the meltblown layer is composed of meltblown polypropylene fibers.

In the various configurations of the invention where selected materials or components, such as the barrier flaps 62 and/or 84, are configured to be permeable to gas while having a resistance and limited permeability to aqueous liquid, the liquid resistant material can have a construction which is capable of supporting a hydrohead of at least about 45 cm of water substantially without leakage therethrough. A suitable technique for determining the resistance of a material to liquid penetration is Federal Test Method Standard FTMS 191 Method 5514, dated 31 Dec. 1968. Backsheet 30 may be composed of a liquid permeable material, but preferably comprises a material which is configured to be substantially impermeable to liquids. For example, a typical backsheet can be manufactured from a thin plastic film, or other flexible liquid-impermeable material. Such "flexible" materials are compliant and will readily conform to the general shape and contours of the wearer's body. Backsheet 30 can help prevent the exudates contained in absorbent structure 32 from wetting articles such as bedsheets and overgarments which contact diaper 10.

In particular embodiments of the invention, backsheet 30 is a polyethylene film having a thickness of from about 0.012 millimeters (0.5 mil) to about 0.051 millimeters (2.0 mil). In the shown embodiment, for example, the backsheet is a film having a thickness of about 0.032 mm (about 1.25 mil). Alternative constructions of the backsheet may comprise a woven or non-woven fibrous web layer which has been totally or partially constructed or treated to impart a desired level of liquid impermeability to selected regions of the backsheet that are adjacent or proximate the absorbent body. For example, a clothlike backsheet may be composed of an approximately 0.5 osy (about 17.7 g/m$^2$) basis weight, polypropylene spunbond fabric which is laminated and thermally bonded to a stretch-thinned polypropylene film having a thickness of about 0.0006 in (about 0.015 mm) and a film basis weight of about 14.5 g/m$^2$. Backsheet 30 typically provides the outer cover of the article. Optionally, however, the article may comprise a separate outer cover member which is in addition to the backsheet.

Backsheet 30 may optionally include a micro-porous, "breathable" material which permits vapors to escape from absorbent structure 32 while still preventing liquid exudates from passing through the backsheet. For example, the breathable backsheet may be composed of a microporous polymer film or a nonwoven fabric which has been coated or otherwise treated to impart a desired level of liquid impermeability. For example, a suitable microporous film is a PMP-1 material, which is available from Mitsui Toatsu Chemicals, Inc., a company having offices in Tokyo, Japan; or an XKO-8044 polyolefin film available from 3M Company of Minneapolis, Minn. The backsheet can also be embossed or otherwise provided with a matte finish to exhibit a more aesthetically pleasing appearance.

The size of backsheet 30 is typically determined by the size of absorbent structure 32 and the exact diaper design selected. Backsheet 30, for example, may have a generally T-shape, a generally I-shape or a modified hourglass shape, and may extend beyond the terminal edges of absorbent structure 32 by a selected distance, such as a distance within the range of about 1.3 centimeters to 2.5 centimeters (about 0.5 to 1.0 inch), to provide side margins.

Topsheet 28 and backsheet 30 are connected or otherwise associated together in an operable manner. As used therein, the term "associated" encompasses configurations in which topsheet 28 is directly joined to backsheet 30 by affixing topsheet 28 directly to backsheet 30, and configurations wherein topsheet 28 is joined to backsheet 30 by affixing topsheet 28 to intermediate members which in turn are affixed to backsheet 30. Topsheet 28 and backsheet 30 can be affixed directly to each other in selected regions, such as in areas along the diaper periphery, by attachment means (not shown), such as an adhesive, sonic bonds, thermal bonds or any other attachment means known in the art. For example, a uniform continuous layer of adhesive, a patterned layer of adhesive, a sprayed pattern of adhesive or an array of separate lines, swirls or spots of construction adhesive may be used to affix topsheet 28 to backsheet 30. It should be readily appreciated that the above-described attachment means may also be employed to interconnect and assemble together the various other component parts of the article described herein.

In the representatively shown embodiment of the invention, the topsheet layer 28 is disposed and secured in facing relation with the backsheet layer 30 to retain and hold the retention portion 48 and the surge management 46 between the backsheet layer and the topsheet layer. The marginal side regions of topsheet layer 28 are operably connected to corresponding marginal side regions of the backsheet layer 30. Each of the attached marginal side regions of the topsheet and backsheet layers is located laterally outboard of its corresponding, associated side edge region of the surge management portion 46. In particular configurations of the invention, the topsheet 28 can include attached marginal end regions, which are located longitudinally outboard of the end edge regions of the retention portion 48 and/or surge management portion 46. Similarly, the backsheet 30 can include attached marginal end regions, which can be located longitudinally outboard of the end edge regions of the retention portion and/or surge management portion.

Elastic members 34 are disposed adjacent the periphery of diaper 10 along each of the longitudinal side edges 20. The leg elastic members 34 can be connected to either or both of the topsheet and backsheet layers to provide elasticized side margins of the diaper article, and can be arranged to draw and hold diaper 10 against the legs of the wearer to provide elasticized leg bands or leg cuffs. Waist elastic members 42 may also be disposed adjacent either or both of the end edges of diaper 10 to provide elasticized waistbands.

Elastic members 34 and 42 are secured to diaper 10 in an elastically contractible condition so that in a normal under strain configuration, the elastic members effectively contract against diaper 10. The elastic members can be secured in an elastically contractible condition in a number of ways; for example, the elastic members may be stretched and secured while diaper 10 is in an uncontracted condition. Alternatively, diaper 10 may be contracted, for example, by pleating, and the elastic members secured and connected to diaper 10 while the elastic members are in their relaxed or unstretched condition. Still other means, such as heat-shrink elastic material, may be used to gather the garment.

In the embodiment illustrated in FIG. 1, leg elastic members 34 extend essentially along the complete length of intermediate region 16 of diaper 10. Alternatively, elastic members 34 may extend the entire length of diaper 10, or any other length suitable providing the arrangement of elastically contractible lines desired for the particular diaper design. Elastic members 34 and 42 may have any of a variety of configurations. For example, the width of the individual elastic members 34 may be varied from 0.25 millimeters (0.01 inches) to 25 millimeters (1.0 inches) or more. The elastic members may comprise a single strand of elastic material, or may comprise several parallel or non-parallel strands of elastic material, and the elastic members may be applied in a rectilinear or curvilinear arrangement. Where multiple strands are employed, the individual strands may be constructed to provide substantially equal elastic forces, or may be constructed to provide different elastic forces. For example, the individual strands may be of different diameter or other size, or may be configured with different amounts of elongation to thereby provide a gradient or other variation of elastic tensions. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 10 with selected patterns of hotmelt or other type of adhesive. For example, sprayed or swirled adhesive patterns may be employed.

In the illustrated embodiments of the invention, for example, leg elastic members 34 may comprise a carrier sheet to which are attached a grouped set of elastics composed of a plurality of individual elastic strands. The elastic strands may intersect or be interconnected, or be entirely separated from one another. The shown carrier sheet may, for example, comprise a 0.002 cm thick film of unembossed polypropylene material. The shown elastic strands can, for example, be composed of LYCRA elastomer which is available from DuPont. Each elastic strand can typically be within the range of about 470–1880 decitex (dtx), and desirably, is about 940 dtx or the equivalent in an embodiment of the invention wherein 3–4 strands are employed for each elasticized legband. Another example of suitable elastic strands can be composed of GLOSPAN elastomer which is available from Globe Manufacturing Co. Each elastic strand can typically be within the range of about 240–1920 denier (den), and desirably, is about 1400 den or the equivalent, in an embodiment of the invention wherein 3–4 strands are employed for each elasticized legband.

In addition, leg elastics 34 may be generally straight or optionally curved. For example, the curved elastics can be inwardly bowed toward the longitudinal centerline of the diaper. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may be offset by a selected distance toward either the front or rear waistband of the diaper to provide desired fit and appearance.

Conventional articles have incorporated various barrier flap structures at their waistband and/or legband regions. For example, such articles have typically incorporated a single or multi-layer piece of material, such as polymer films and film-nonwoven laminates, at the waistband portion of the article along the lateral cross-direction to form a waist flap or dam. The materials, however, typically exhibit similar behavior. When the materials are stretched, they have a tendency to neck down, thereby reducing their effective widths. As they neck down, they tend to form relatively large corrugations or furrows which extend substantially along the direction of stretching. The presence of such corrugations can cause the barrier flaps, particularly the waist flaps, to collapse upon themselves, thereby reducing the ability to remain open to receive and trap bodily waste materials. Additionally, when the conventional materials contract, they tend to decrease in overall stiffness, and this decrease in composite stiffness can again allow the barrier flaps to fold over or collapse upon themselves, thereby reducing their effectiveness.

It has been discovered that particular barrier flap structures, such as laminates incorporating individual and separated elastic strands, can provide structures which can overcome the shortcomings of prior structures. When stretched, the stranded laminates of the invention substantially avoid the undesired stretch-wise corrugating effect typically seen across the plane of the barrier flap and along the intended direction of stretch. Desirably, the amount of stretching does not exceed the amount of elongation at which the elastic strands were assembled into the laminate. When fully stretched and elongated, the stranded laminate can lay substantially flat. As the stranded laminate relaxes and elastically contracts, fine corrugations of sufficient size and frequency can be provided with the furrows or valleys of the corrugate generally aligned to extend substantially perpendicular to the direction of the contraction. The fine corrugations can enhance the stiffness of the flap structure and can improve its ability to remain open to receive waste materials. The stranded laminates of the present invention substantially avoid necking when stretched. Additionally, the geometry of the stranded laminates themselves play an important role in the performance of the materials when employed as a barrier dam structure, such as the shown waist dam. The placement of the strands can also play a role in the functionality of the various configurations of the laminas.

It has been found, however, that the identifications of conventional types of materials or families of materials have not been adequate for deriving waist flap structures that are sufficiently effective and reliable. It has been discovered that the performance and effectiveness of the waist dam is dependent upon particular combinations of properties and behavior characteristics of the materials employed to assemble and construct the composite barrier flaps. For example, the incorporation of a flap composed of a polyurethane film or film laminate at the article waistband, and the placement of a flap composed of a SMS (spunbond-meltblown-spunbond) nonwoven fabric laminate at the article waistband have not reliably provided a sufficiently effective barrier flap structure. It is important to further configure the materials with particular physical properties. One of the desired physical properties is the stiffness of the flap member, and the desired stiffness can be achieved in a variety of ways. For example, contributing factors include the basis weight of the flap materials, the stiffness or modulus of the individual components, the presence of adhesive added to laminas within the flap member, the pattern and distribution of the applied adhesive, the presence of welding or ultrasonic treatments, the number of individual elastic strands employed in the barrier flap structure, the geometry of the strand placement within barrier flap, the presence and alignment of corrugations within the barrier flap, and the number of layers of components incorporated within the barrier flap.

The present invention can provide a distinctive article, such as the diaper 10, which has a cross-wise, lateral dimension 24 and a length-wise, longitudinal dimension 26. The representative diaper 10, has a front waistband portion 12, a rear or back waistband portion 14, and an intermediate portion 16 which interconnects the front and rear waistband portions. The article includes a backsheet layer 30 having a laterally extending width and a longitudinally extending length. A porous, liquid permeable topsheet layer 28 has a laterally extending width and a longitudinally extending length, and is connected in superposed relation to the backsheet layer 30. An absorbent structure, such as the absorbent body 32, is sandwiched and operably secured between the backsheet layer 30 and the topsheet layer 28.

As representatively shown in FIGS. 1, 2 and 3, the diaper 10 can have a waist pocket member 80 which can include a laterally and longitudinally extending flange section 82, and a laterally and longitudinally extending barrier flap or pocket section 84. The flange section can, for example, be connected to the bodyside surface of the topsheet 28. The flap or pocket section 84 of the waist pocket member 80 includes a substantially fixed edge portion 102 which is secured to the article along and immediately adjacent the boundary of the flange section 82, and includes an elasticized, gathered moveable edge portion 104, which is longitudinally spaced from the fixed edge portion 102 by a selected distance. The pocket section thereby provides an operable waist dam and waist flap construction. The pocket section also includes a substantially liquid impermeable pocket barrier layer 106, and a pocket fabric layer 108 which is connected in facing relation with the pocket barrier layer. The pocket fabric may, for example be composed of a woven or nonwoven fabric, and in the shown arrangement, the fabric layer is desirably a nonwoven. A plurality of separate, laterally extending pocket elastic members 110 are sandwiched and operably connected between the pocket barrier layer 106 and the pocket fabric layer 108 to provide an elasticized waist pocket composite 112, which is gathered substantially along the lateral cross-direction 24 and is elastically stretchable at least along the cross-direction. The shown arrangement includes elastics members which are aligned substantially parallel to one another, but optionally can include other separated configurations and alignments of the elastics. Desirably, the fabric layer 108 is arranged for placement against the wearer's skin, although the barrier layer 106 may optionally be appointed for placement immediately adjacent the wearer's skin.

In a particular aspect of the invention, the flange section 82 of the waist pocket member 80 can include a substantially liquid impermeable flange barrier layer 114, and a flange fabric layer 116 which is operably connected and secured in facing relation with the flange barrier layer. The flange fabric may, for example, be composed of a woven or nonwoven fabric, and in the shown arrangement, and the fabric layer is desirably a nonwoven. A plurality of separate, laterally extending flange elastic members 118 are sandwiched and operably connected between the flange barrier layer 114 and the flange fabric layer 116 to provide an elasticized flange composite 120, which is substantially laterally gathered by the flange elastic members and is elastically stretchable at least along the cross-direction 24. The shown arrangement includes elastics members which are substantially parallel to one another, but optionally can include other separated configurations of the elastics which may be non-parallel. Desirably, the fabric layer 116 is arranged for placement against the wearer's skin, although the barrier layer 114 may optionally be appointed for placement immediately adjacent the wearer's skin. Particular configurations of the flange section 82 can be constructed and arranged to be substantially coterminous with its associated end edge margin 22 of the article.

In particular configurations of the invention, such as the arrangements shown in FIGS. 2 and 3, the pocket section 84 of the waist pocket member 80 can be integrally formed with the flange section 82 of the waist pocket member. In these arrangements, the pocket barrier layer 106 is integrally formed with the flange barrier layer 114 to provide a combined, flange-pocket barrier layer, and the fabric pocket layer 108 is integrally formed with the fabric flange layer 116 to provide a combined flange-pocket fabric layer. The representatively shown arrangement, further includes a flange-pocket barrier layer which is substantially coextensive with the flange-pocket fabric layer.

In other arrangements of the invention, the elastic members 118 in the flange section 82 are spaced from the closest elastic members 110 in the pocket section 84 by a predetermined boundary space 122 which provides a separation distance of at least about 2 mm. In particular aspects, the separation distance provided by the boundary spacing distance is at least about 8 mm, and optionally is at least about 16 mm. The separation distance provides an amount of isolation which effectively permits the flange elastic members to operate substantially separately from the pocket elastic members. Accordingly, the gathering provided by the flange elastics can be substantially separated from the gathering provided by the pocket elastics.

Figure 4:
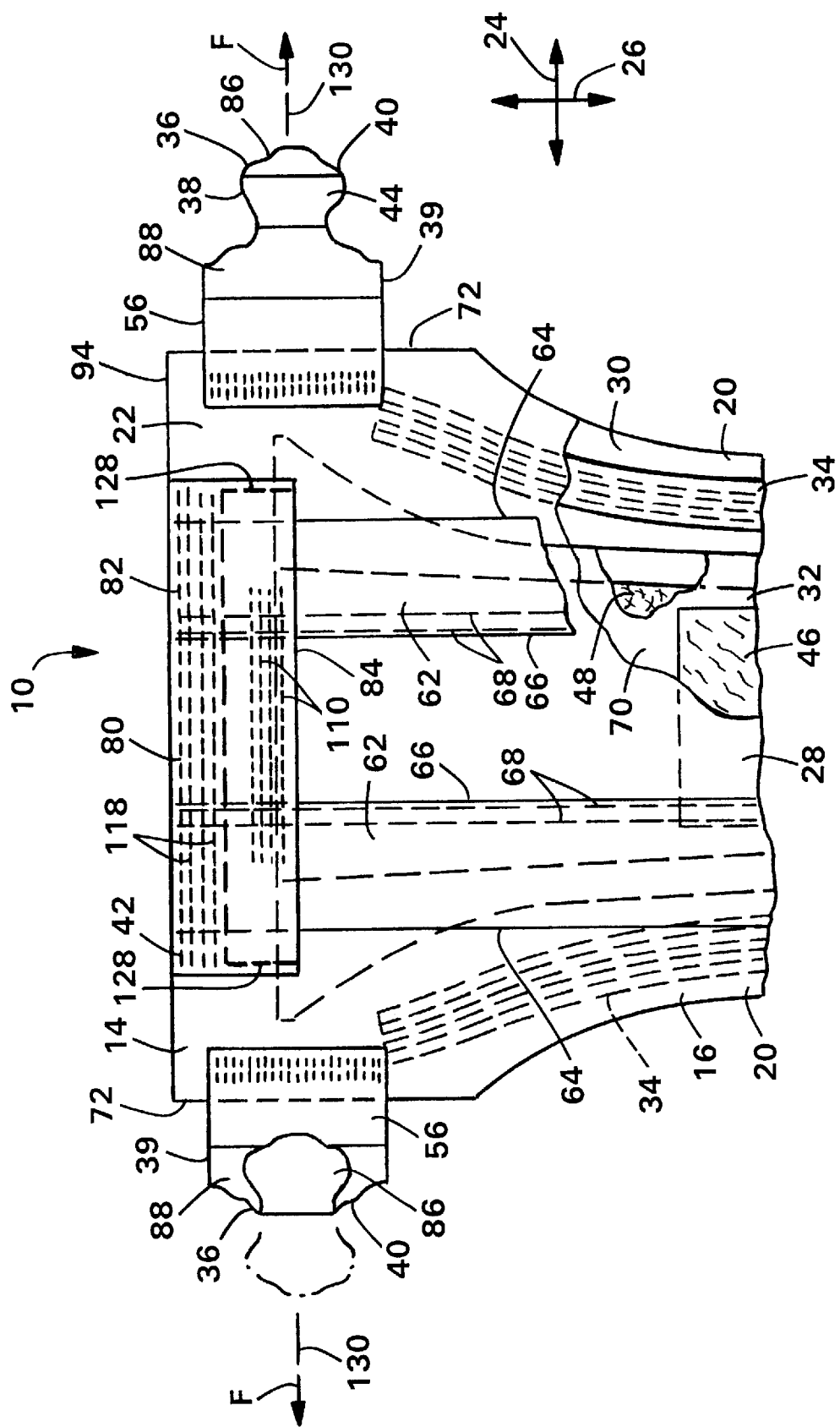
FIG. 4 representatively shows an enlarged, top view of a waistband section of the article of the invention.

With reference to FIG. 4, the fastener tabs 36 at the laterally opposed sides of the diaper 10 are desirably substantially aligned along a central, cross-directional alignment line 130. In particular aspects of the invention, the alignment line 130 substantially coincides with, and lies within, the boundary space 122 which separates the set of pocket section elastics 110 from the set of flange section elastics 118 within the waist pocket member 80. In desired configurations, the distal, terminal edge 105 of the pocket section can be aligned with or positioned relatively close to a central force line 130 which is created when a tensioning force, F, is applied to the fastening tabs. Having the distal edge generally aligned with the force line 130 can operably stretch the pocket section 84, particularly the movable edge portion 104 of the pocket section, and can cause the pocket section to stand away from the article. In particular, the pocket section can be more effectively urged to stand away from the bodyside surface of the topsheet 28 during use to create a more effective pocket or waist flap structure to capture bodily fluids and waste. Additionally, the flap structure of the waist pocket section 84 can more effectively maintain contact with the body throughout a range of motions produced by the wearer, and can provide an improved gasket at the region of the movable edge portion 104.

With reference again to FIG. 2, another aspect of the invention can include a configuration in which a one of the elastic members 110 in the pocket section 84 is located most proximally adjacent to the substantially fixed edge portion 102. In addition, such adjacent elastic member is located between the substantially fixed edge portion 102 and the moveable edge portion 104 of the pocket section, and is spaced from the substantially fixed edge portion 102 of the pocket section by a proximal spacing distance 124 which is not less than about 2 mm, and optionally is not less than about 4 mm. In further aspects of the invention the proximal spacing distance 124 is not more than about 13 mm, and optionally is not more than about 8 mm. The proper selection of the spacing distance 124 can help the pocket section 84, particularly its movable edge region, maintain an open position spaced-away from the topsheet of the article. If the distance is too small, the pocket section may not open reliably. If the distance is too great, the pocket section may not adequately resist excessive collapsing.

Figure 6:
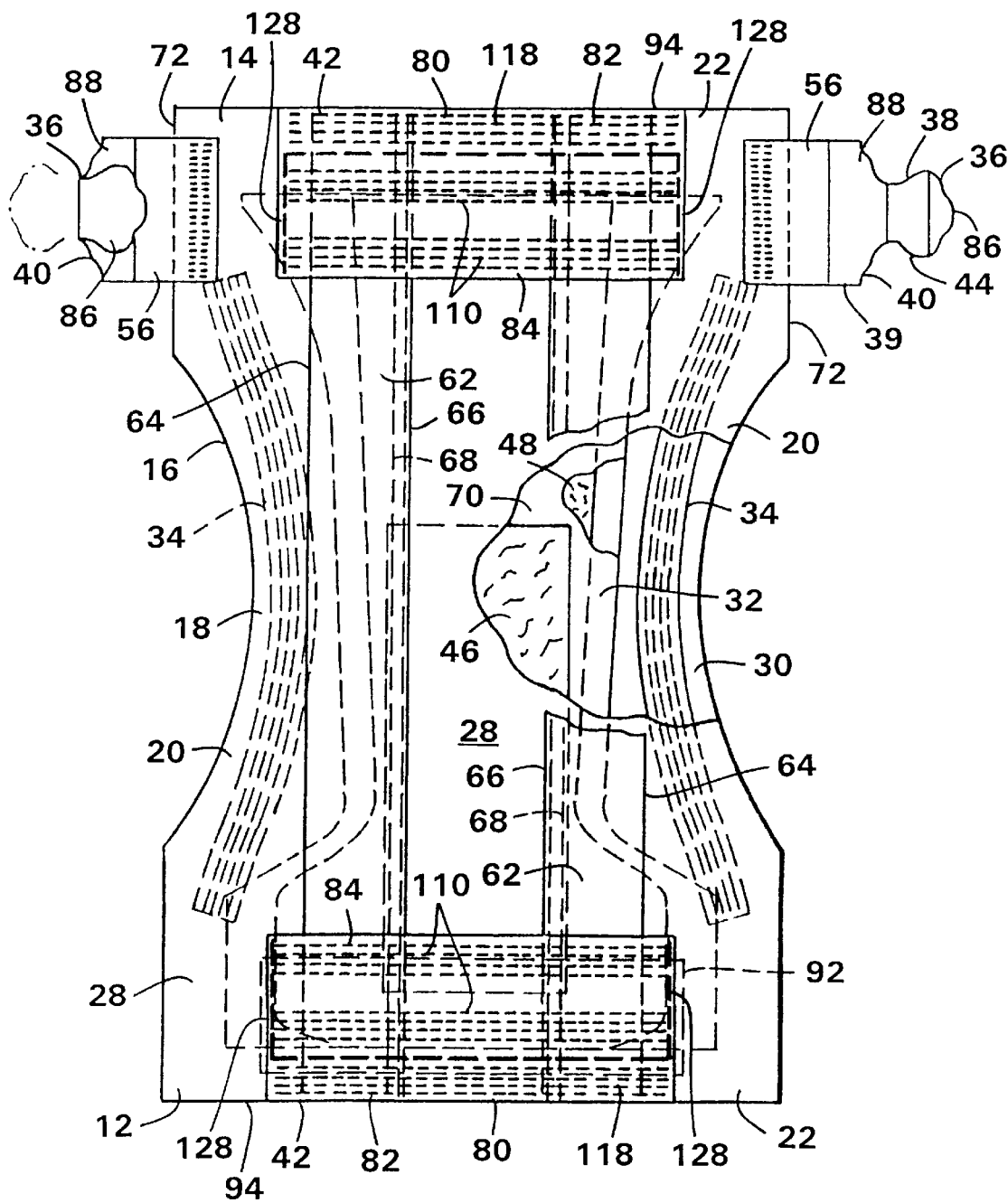
FIG. 6 representatively shows a partially cut-away, top view of another article having dual groupings of elastic strands in the pocket section of the barrier flap system of the invention.

With reference to FIGS. 2 and 3, the pocket section 84 of the waist pocket member 80 can be secured to an appointed region of the article, such as the topsheet 28, by a region of attachment 126. In the shown, arrangement, the attachment 126 extends out of the boundary space 122 to secure the flange section 82 to the topsheet. Optionally, the attachment 126 can be substantially restricted to the boundary space 122, at least within a section of the boundary space 122 which is in a laterally middle or medial portion of the article, and a separate attachment can secure the flange section 82 to the article. Accordingly, the attachment region 126 can operably provide the substantially fixed edge portion 102 of the pocket section 84. In addition, the pocket section 84 of the waist pocket member 80 has laterally opposed end sections 128 which are secured to lie substantially flat against the topsheet 28. As a result, the pocket section 84 of the waist pocket member can be secured to the topsheet 28 with a generally U-shaped arrangement of attachment (FIGS. 1, 4 and 6).

Figure 5:
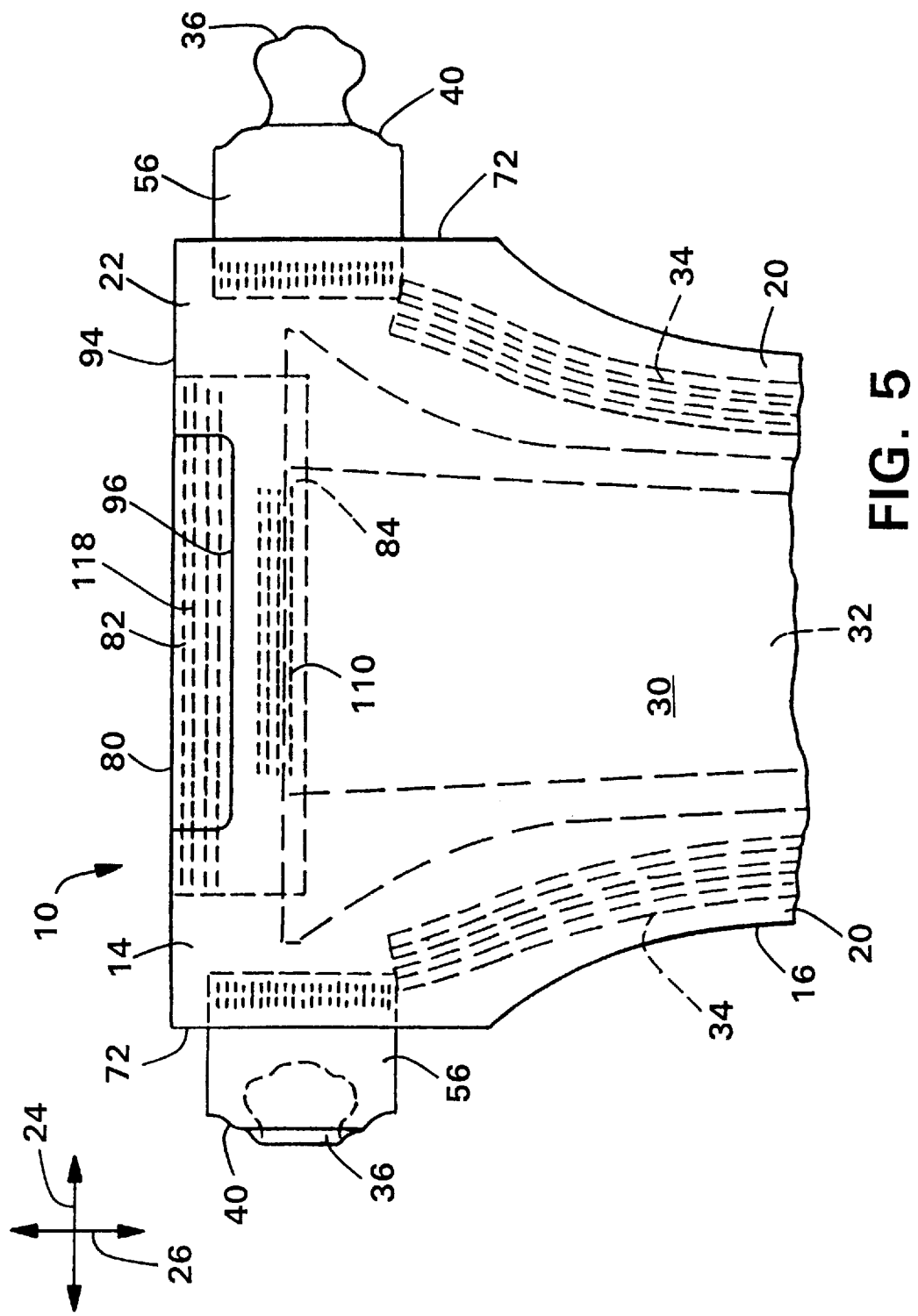
FIG. 5 representatively shows an enlarged, top view of another waistband section of the article of the invention having a notch formed into the waistband of the backsheet.

With reference to FIG. 5, particular configurations of the invention can have the backsheet layer 30 constructed with at least one longitudinally terminal waistband edge 94 which has an inwardly extending notch region 96 formed therein. The flange section 82 of the waist pocket member 80 is configured and arranged to span across the notch region 96. In addition, the marginal edge portions of the backsheet which are immediately adjacent the notch section can be operably connected and attached to corresponding portions of the flange section.

In the various configurations of the invention, the waistband notch region 96 can have a variety of shapes and sizes. The notch region can have a curvilinear shape, a rectilinear shape, or combinations thereof. Desirably, the waistband notch region 96 can be substantially laterally centered in the cross-directional, medial region of the backsheet 30. In the various arrangements of the invention, the cross-directional extent of the notch region 96 is not more than about 80% of the overall, cross-directional extent of the total article, and desirably is not more than about 40% of the overall, cross-directional extent of the article to provide improved performance. In addition, the cross-directional extent of the notch region 96 can be not less than about 10% of the overall, cross-directional extent of the article, and desirably is not less than about 20% of the overall, cross-directional extent of the article to provide desired levels of comfort and waste containment. In still other aspects, the longitudinal or depth extent of the notch region 96 is within the range of about 2–15% of the overall longitudinal extent of the total article. In a diaper-type article, for example, the notch region 96 can have a maximum, longitudinally inward extent of at least about 9 mm. Alternatively, the inward extent of the notch region 96 is at least about 12.5 mm, and optionally is at least about 15 mm. In other arrangements, the inward extent of the notch region 96 is not more than about 65 mm. Alternatively, the maximum inward extent can be not more than about 55 mm, and optionally can be not more than about 45 mm. When measuring the dimensions of the notch region 96, the article is placed in its substantially flat-out, uncontracted condition with the elastic gathers at the article waistband substantially removed.

With reference to FIGS. 2 and 3, a one of the pocket elastic members 110 is located most proximally adjacent to the terminal edge 105 of the moveable edge portion 104 of the pocket section 84 and is spaced from the terminal edge by a spacing distance 107 of not more than about 13 mm. Alternatively, the edge spacing distance is not more than about 7 mm, and optionally is not more than about 1 mm. In a further aspect, the terminal edge 105 is substantially unfolded. In particular, the terminal edge portion of the pocket section is not folded back upon itself to envelop and enclose one or more of the pocket elastics. The positioning of elastic members proximate the distal, terminal edge 105 can help to maintain the open position of the pocket section 84 across substantially the full width of the pocket section. As a result, the pocket section can better provide a functional barrier dam structure.

The various arrangements of the invention can also be constructed to provide the flange and pocket sections 82 and 84, respectively, with desired stiffness values. In particular, either or both of the flange and pocket sections can have a stiffness value which is at least about 5 mg. Alternatively, the stiffness can be at least about 15 mg, and optionally, can be at least about 30 mg to provide improved performance. In other aspects of the invention, either or both of the flange and pocket sections can have a stiffness which is not more than about 250 mg. Alternatively, the stiffness can be not more than about 200 mg, and optionally, can be not more than about 170 mg to provide improved performance. Where the stiffness is too low, the pocket section can be excessively susceptible to collapsing. Where the stiffness is too high, the pocket or flange sections may cause excessive irritation to the wearer.

The stiffnesses of the flange and pocket sections of the waist pocket member 80 can be determined by employing the test methodology of TAPPI T543 om-94, and by employing a Gurley Digital Stiffness tester, Model 4171-D, a device available from Teledyne Gurley, a business having offices located in Troy, N.Y. The stiffnesses can be expressed as milligrams (mg) which correspond to Standard Gurley Units of milligrams-force. Accordingly, the stiffness values of the various sections of the waist pocket member 80 are bending stiffnesses. For the purposes of the present invention, the axis about which a bending moment is applied to the sample during the stiffness testing is a bending axis which is aligned substantially parallel to the direction of elastic stretch and gathering provided by the associated elastic members, such as elastic members 110 and/or 118. With regard to the stiffness testing of the pocket section 84, for example, the bending axis of the test sample of the pocket section would be along an axis line which would have been substantially aligned with the article cross-direction 24, as observed when the pocket section was originally assembled in the article.

In regard to either or both of the flange section 82 and pocket section 84 of the waist pocket member 80, the barrier layer can be provided by polymer films or fabrics having low permeability to liquid, and combinations thereof. Polymer films may, for example, be composed of polyolefins, polyesters, polyamides and the like. Nonwoven materials can include spunbond-meltblown-spunbond (SMS) fabrics, meltblown fabrics, calendered nonwoven sheets and the like. With respect to the passage of liquid through its thickness, the barrier layer is constructed to exhibit a hydrohead of resistance which is sufficient to provide an effective barrier against the passage liquids, such as urine.

For example, the barrier layer may be composed of a 0.0006 inch (0.015 mm) cast, embossed film, such as a CT (XEM400.1), or a 0.0004 inch (0.010 mm) blown film, such as XSF-367, available from Consolidated Thermoplastics, a business having offices located in Chippewa Falls, Wis. The barrier layer may also be a 0.00035 inch (0.0089 mm) stretch-thinned film, such as XP1024A, available from Edison Plastics a business having offices located in Macalester, Okla.

With regard to either or both of the flange section 82 and pocket section 84 of the waist pocket member, the fabric layers 108 and/or 116 can be composed of a fine denier, low basis weight nonwoven material. Examples of such nonwoven fabrics include polypropylene spunbond materials, bicomponent polypropylene/polyethylene spunbond materials, meltblown materials, SMS materials, through-air-bonded carded webs, point-bonded bonded-carded webs, and the like.

For example, the fabric layer may comprise a 0.5 osy (17 gsm) polypropylene spunbond fabric composed of fibers having denier of less than about 4 den. The fabric layer can alternatively have fibers with deniers of less than about 3 den, and optionally can include fibers having deniers of less than about 2.5 den.

Either or both of the pocket elastic members 110 and flange elastic members 118 can be composed of strands of natural or synthetic elastomeric materials, such as natural or synthetic rubbers. In particular aspects of the invention, the elastic members can include strands having a denier of not less than about 100 denier. Alternatively, the elastic members can have a denier of not less than about 280, and optionally can have a denier of not less than about 360. In other aspects of the invention, the elastic members can include strands having a denier of not more than about 1920 den. Alternatively, the elastic members can have a denier of not more than about 1140 den, and optionally can have a denier of not more than about 560 den. For example, the pocket elastic members 110 and/or the flange elastic members 118 can include 360 denier GLOSPAN S7 elastic strands available from Globe Manufacturing Co.

To produce the flange and pocket sections of the waist pocket member 80, the pocket elastics and/or the flange elastics can be elongated 50–350 percent (as determined with respect to the unstretched length of the elastics) prior to assembly into the waist pocket member to form the pocket composite 112 and/or the flange composite 120. For example, the flange elastics 118 can be configured with about 150 percent elongation, and the pocket elastics 110 can have an elongation of about 175 percent.

The number of elastic strands and the spacing between the strands can be selected and arranged to provide desired performance. For example, the elastics can be selectively configured to provide a desired gasketing function against the wearer's skin while avoiding excessive irritation and redmarking of the wearer's skin.

In particular aspects of the invention, the number of elastic strands in each of the flange section 82 and/or pocket section 84 can be at least about 2, and alternatively is at least about 3. In further aspects of the invention, the number of elastic strands in each of the flange section and/or pocket section can be not more than about 25. Alternatively, the number of elastic strands in each of the sections can be not more than about 20, and optionally can be not more than 15. Laminates with too many strands across the longitudinal depth of the pocket section can undesirably cause the flap structure to lay closed, substantially flat against the topsheet of the article, while laminates having too few strands can excessively collapse and fold in upon themselves. The appropriate number of strands, the appropriate spacing between strands, and the appropriate spacing of the strands from the fixed and movable edges of the pocket section are dependent upon the physical properties of the individual laminate components, as well as the dimensions of the flaps.

In other aspects of the invention, the elastic members of the flange section 82 and/or pocket section 84 can have an elastic spacing distance 132 which is at least about 2 mm. Alternatively, the elastics spacing distance 132 can be at least about 3 mm, and optionally can be at least about 4 mm. In further aspects, the elastic members of the flange section 82 and/or pocket section 84 can have an elastic spacing distance 132 which not more than about 13 mm. Alternatively, the elastics spacing distance 132 can be not more than about 11 mm, and optionally can be not more than about 8 mm to provide improved control over the operation of the barrier flap structure.

To further control the operation of the barrier flap structure, such as the pocket section 84, The pocket elastic members 110 may be uniformly spaced across the entire width of the lamina ( as determined along a dimension which is substantially perpendicular to the stretching dimension of the elastic member), or they may be grouped into discrete and distinct functional sets. For example, FIG. 6 representatively shows a laminate having more than one functional groupings of pocket elastics 110. Such multiple grouping may be placed in either or both of the pocket or flange sections of the waist pocket member 80 to control the operation of the barrier flap and to enhance performance.

In particular aspects of the invention, the flange elastic members 118 can be arranged to provide for a flange contractive force and the pocket elastic members can be arranged to provide for pocket contractive force. In a particular aspect of the invention, the contractive force exerted by the flange elastics is configured to be relatively greater than the contractive force exerted by the pocket elastics. As representatively shown in FIGS. 1 and 4, for example, the flange elastics can be longer, or otherwise larger or more strongly contracted, than the pocket elastics. Such an arrangement can provide a desired relative contraction between the flange and pocket sections of the waist pocket member 80 when the waist pocket is operably assembled to the final article, and can help maintain a desired, open condition of the pocket section 84 during use on the wearer.

In a desired aspect of the invention, the elastic members in either the waist flange, pocket or both regions may be operably zone-tensioned, as representatively shown in FIGS. 1 and 4. The zone tensioning may be achieved in a variety of ways. For example, an adhesive or other bonding mechanism may be applied only in the areas where the retraction of the elastic members is intended to gather the flap composite. In the regions where the bonds are absent, the remaining elastic members can contract substantially without gathering the flap composite. Alternatively, other techniques, such as ultrasonics, can be employed to operably deaden the elastic members in the regions where elastic retraction is not desired.

The elastomeric members 110 and/or 118 can be attached to either or both of their associated barrier and fabric layers with a suitable securing means, such as a selected pattern of adhesive or other type of bonding. For example, the adhesive may be applied by spraying adhesive discontinuous droplets or filaments, and/or may be applied by arranging generally continuous lines of adhesive in a selected pattern, such as a swirl pattern. Alternatively, the elastomeric members 110 and/or 118 can be attached to at least one of the barrier and fabric layers with a plurality of individual, longitudinally extending strips of adhesive. Each individual adhesive strip is spatially separated from immediately adjacent adhesive strips by a discrete distance, and each individual adhesive strip is arranged to attach substantially an individual one of the elastomeric members to the at least one of the barrier and fabric layers. In the shown arrangements, for example, the strips of adhesive can be aligned substantially parallel to one another.

With reference to FIGS. 1 and 4, the pocket section 84 of the waist member 80 may be configured to bridge and span over the inward facing , bodyside surfaces of the longitudinally extending containment flaps 62. Desirably, the movable edge portions 104 of the pocket section 84 are substantially unconnected and unattached to the distal, movable edges 66 of the containment flaps 62 to thereby reduce interaction between the elasticized containment flaps 62 and the elasticized pocket section 84. In addition, it is desirable to zone the elastic tension exerted by the elastic members 68 employed to elasticize the containment flaps 62. More particularly, the elastic tension in the containment flaps is substantially restricted to a longitudinally medial section of each containment flap. Accordingly, the end regions of each containment flap, particularly the end regions generally adjacent to the pocket section 84, are substantially free of elastic tension exerted by the elastic members 68. The distal edges 66 can also be secured to the topsheet layer 28 with a suitable attaching mechanism to further isolate the distal edges 66 of the containment flaps away from the operation and opening of the pocket section 84.

The above-described zoned tensioning of the containment flaps 62 can be achieved in a variety of ways. For example, the elastic contractibility of the elastic members 68 in the appropriate end regions of the containment flaps can be operably deadened, such as by a mechanical, ultrasonic or thermal treatment which effectively "kills" or otherwise deactivates the elasticity or contractibility in the selected regions. Alternatively, the elastic members 68 in the end regions of the containment flaps may be substantially unattached to the containment flap material. Accordingly, the elastic members at the containment flap end regions can elastically retract substantially without exerting a gathering tension onto the end regions of the containment flaps 62. In further configurations, the distal end regions of the containment flaps can be substantially, entirely immobilized, such as by operably securing the end regions onto the topsheet layer 28 with adhesive, sonic bonds or other attaching mechanisms.

In the various arrangements of the invention, the selected absorbent body, such as provided by the absorbent structure 32, is positioned and operably secured between the topsheet 28 and the backsheet 30 to form the diaper 10. The absorbent body has a construction which is generally compressible, conformable, non-irritating to the wearer's skin, and capable of absorbing and retaining liquid body exudates. It should be understood that, for purposes of this invention, the absorbent structure may comprise a single, integral piece of material, or alternatively, may comprise a plurality of individual separate pieces of material which are operably assembled together. Where the absorbent structure comprises a single, substantially integral piece of material, the material could include the desired structural features formed into selected spatial regions thereof. Where the absorbent structure comprises multiple pieces, the pieces may be configured as discrete layers or as other nonlayered shapes and configurations. Furthermore, the individual pieces may be coextensive or non-coextensive, depending upon the requirements of the product. It is preferred, however, that each of the individual pieces be arranged in an operable, intimate contact along at least a portion of its boundary with at least one other adjacent piece of the absorbent structure. Preferably, each piece is connected to an adjacent portion of the absorbent structure by a suitable bonding and/or fiber entanglement mechanism, such as ultrasonic or adhesive bonding, or mechanical or hydraulic needling.

In the representatively shown embodiments, absorbent structure 32 has a liquid-acquisition zone, a target zone, and a contoured, curvilinear periphery, particularly along its side edges. The two generally mirror-image, inwardly bowed, lateral edges provide for a narrower intermediate section suitable for positioning in the crotch of the wearer. In the shown absorbent structure 32, a front section thereof includes two transversely spaced ear regions and a central region. The target zone encompasses the area where repeated liquid surges typically occur in absorbent structure 32. When the diaper is worn, the ear regions are configured to generally engage the sides of the wearer's waist and torso, and central region is configured to generally engage the medial portion of the wearer's waist and torso.

Absorbent structure 32 may be manufactured in a wide variety of sizes and shapes (for example, rectangular, trapezoidal, T-shape, I-shape, hourglass shape, etc.) and from a wide variety of materials. The size and the absorbent capacity of absorbent structure 32 should be compatible with the size of the intended wearer and the liquid loading imparted by the intended use of the absorbent article. Further, the size and the absorbent capacity of absorbent structure 32 can be varied to accommodate wearers ranging from infants through adults. In addition, it has been found that with the present invention, the densities and/or basis weights of the respective surge management 46 and retention 48 portions, as well as their relative ratios, can be varied. In a particular aspect of the invention, the absorbent structure has an absorbent capacity of at least about of synthetic urine. Alternatively, the absorbent structure can have an absorbent capacity of at least about 400 gm of synthetic urine to provide improved performance.

Various types of wettable, hydrophilic fibrous material can be used to form the component parts of absorbent structure 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials used for the surge management portion 46 can be provided by a CAHN, SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

Retention portion 48 can comprise a matrix of hydrophilic fibers, such as a web of cellulosic fluff, mixed with particles of high-absorbency material. In particular arrangements, retention portion 48 may comprise a mixture of superabsorbent hydrogelforming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-stepwise gradient through a substantial portion of the thickness (z-direction) of the absorbent structure, with lower concentrations toward the bodyside of the absorbent structure and relatively higher concentrations toward the outerside of the absorbent structure. Suitable z-gradient configurations are described in U.S. Pat. No. 4,699,823 issued Oct. 13, 1987 to Kellenberger et al., the disclosure of which is incorporated herein by reference in a manner that is consistent with the present description. The superabsorbent particles may also be arranged in a generally discrete layer within the matrix of hydrophilic fibers or may be configured as discrete, separate pocket regions of superabsorbent material. In addition, two or more different types of superabsorbent may be selectively positioned at different locations within or along the fiber matrix.

The high-absorbency material may comprise absorbent gelling materials, such as superabsorbents. The absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent structure include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28,1978 to Masuda et al. and U.S. Pat. No. 4,286,082 issued Aug. 25,1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in retention portion 48 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in retention portion 48.

Preferred for use are particles having an average size of from about 20 microns to about 1 millimeter. "Particle size" as used herein means the weighted average of the smallest dimension of the individual particles.

Suitable high-absorbency materials can have particular characteristics of Absorbent Capacity (sometimes referred to as "AC"), Deformation Under Load (sometimes referred to as "DUL"), and the Wicking Index (sometimes referred to as "WI"). These parameters are described in detail in U.S. patent application Ser. No. 757,787 of S. Byerly et al., entitled ABSORBENT COMPOSITES AND ABSORBENT ARTICLES CONTAINING SAME and filed on Sept. 11, 1991 (Attorney Docket No. 10,174), the disclosure of which is hereby incorporated by reference in a manner that is consistent with the present specification.

In a particular aspect of the invention, absorbent retention portion 48 comprises a matrix of substantially hydrophilic fibers having a quantity of high-absorbency material distributed therein. Selected superabsorbent polymers having improved absorbent properties can be important for maximizing the performance while retaining the desired thinness of the absorbent article. To provide improved performance, the particles of superabsorbent material can be selected to provide an absorbency-under-load (AUL) value which is within the range of about 25–40, and provide a Absorbent Capacity (AC) value which is within the range of about 32–48. The rate of liquid uptake by the superabsorbent material is within the range of about 3–15 g/g (grams liquid per gram superabsorbent) at 30 seconds of absorbency under load, 6.5–21 g/g at 5 minutes absorbency under load and 25–40 g/g at 60 minutes absorbency under load.

A suitable method for determining AUL is described in detail in U.S. Pat. No. 5,147,343 of S. Kellenberger, granted Sept. 15, 1992 and entitled ABSORBENT PRODUCTS CONTAINING HYDROGELS WITH ABILITY TO SWELL AGAINST PRESSURE (Attorney Docket No. 8786.1); and also published Nov. 2, 1989 as European Patent Application No. EP 0 339 461 A1; the disclosure of which is hereby incorporated by reference in a manner that is consistent with the present specification.

An example of superabsorbent polymer suitable for use in the present invention is SANWET IM 3900 polymer available from Hoechst Celanese, a business having offices in Portsmouth, Va. Other suitable superabsorbents may include DOW DRYTECH 2035LD polymer obtained from Dow Chemical Co., a business having offices in Midland, Mich.; or FAVOR SAB 870M polymer available from Stockhausen, Inc., a business having offices in Greensboro, N.C.

The matrix of hydrophilic fibers comprising retention portion 48 may be a layer of cellulosic wood pulp fluff, and the particles of superabsorbent polymer can be distributed within the matrix of hydrophilic fibers. The hydrophilic fibers and high-absorbency particles can be provided in a fiber-to-particle ratio which is not more than about 75:25, alternatively, is not more than about 70:30, and optionally, is not more than about 55:45, by weight. In further aspects of the invention, the fiber-to-particle ratio is not less than about 25:75, preferably is not less than about 30:70 and more preferably is not less than about 45:55, by weight. Such fiber-to-particle ratios can be particularly desirable in the target zone of the absorbent structure. In particular embodiments of the invention, the fiber-to-particle weight ratio is not more than about 65:35 and is not less than about 50:50 to provide desired performance.

The hydrophilic fibers and high-absorbency particles can form an average composite basis weight which is within the range of about 400–900 gsm. Again, such basis weight is particularly desirable in the target zone of the absorbent structure. In certain aspects of the invention, the average composite basis weight is within the range of about 500–800 gsm, and preferably is within the range of about 550–750 gsm to provide desired performance.

To provide the desired thinness dimension to the various configurations of the absorbent article of the invention, retention portion 48 can be configured with a bulk thickness which is not more than about 0.6 cm. Preferably, the bulk thickness is not more than about 0.53 cm, and more preferably is not more than about 0.5 cm to provide improved benefits. The bulk thickness is determined under a restraining pressure of 0.2 psi (1.38 kPa).

The density of retention portion 48 or other component of the absorbent article can be calculated from its basis weight and thickness. With respect to diapers, for example, the weight and thickness are measured on newly unpacked, unfolded and dry diapers at a restraining pressure of 0.2 psi (1.38 kPa). Conventional thickness measuring devices may be employed to determine the thickness needed to calculate the density.

In the illustrated embodiments of the invention, absorbent retention portion 48 includes 4–22 grams of wood pulp fluff, preferably includes about 8–18 grams of fluff and more preferably includes about 12–14 grams of fluff to provide desired benefits. The wood pulp fluff generally provides shape and form to diaper 10, and carries and positions the particles of superabsorbent polymer or other high-absorbency material. Retention portion 48 can contain about 7–12 grams of superabsorbent polymer, and in the shown embodiment, contains about 8 grams of superabsorbent polymer. Sufficient superabsorbent polymer is incorporated into retention portion 48 to provide an adequate total absorbent capacity of at least about 300 gm of synthetic urine. For example, a medium size diaper for an infant weighing about 16–28 lb (about 7–13 kg) can typically have a total retention capacity of about 400 grams of synthetic urine.

The fluff and superabsorbent particles can be selectively placed into desired zones of retention portion 48. For example, the fluff basis weight may vary across the width dimension of retention portion 48. Alternatively, relatively larger amounts of fluff may be positioned toward the front waistband end of the retention portion. For example, see U.S. Pat. No. 4,585,448 issued Apr. 29, 1986, to K. Enloe. In the illustrated embodiment, the majority of the superabsorbent material may be distributed down a medial region of retention portion 48 which extends along the length dimension of the retention portion and measures about 3.5–4.5 inches (about 8.9–11.4 cm) in width. In addition, the superabsorbent material may have a selected zoned placement to reduce the amount of superabsorbent material located proximate the side and end edges of the retention portion. The reduced amounts of superabsorbent material at the edges of the retention portion can improve the containment of the superabsorbent particles within the fibrous fluff matrix of retention portion 48. The pulsed, zoned placement of the superabsorbent material can, for example, be achieved by the method and apparatus described in U.S. Pat. No. 5,028,224 to C. Pieper et al., entitled METHOD AND APPARATUS FOR INTERMITTENTLY DEPOSITING PARTICULATE MATERIAL IN A SUBSTRATE and issued Jul. 2, 1991 (Attorney Docket No. 8761), the disclosure of which is hereby incorporated by reference in a manner that is consistent herewith.

In a particular aspect of the invention, absorbent structure 32 can be generally T-shaped with the laterally extending cross-bar of the "T" generally corresponding to the front waistband portion of the absorbent article for improved performance, especially for male infants. In the illustrated embodiments, for example, the retention portion across the ear section of the front waistband region of the article has a cross-directional width of about 9.0 inches (about 22.9 cm), the narrowest portion of the crotch section has a width of about 3.5 inches (about 8.9 cm) and the back waistband region has a width of about 4.5 inches (about 11.4 cm).

The entire absorbent structure 32, or any individual portion thereof, such as the retention portion, can be overwrapped in a hydrophilic high wet-strength envelope web, such as a high wet-strength tissue or a synthetic fibrous web. Such overwrapping web can also increase the in-use integrity of the absorbent structure. The web can be suitably bonded, such as with adhesive, to absorbent structure 32 and to other components of the product construction.

Due to the high concentrations of superabsorbent particles, or other high-absorbency material, in retention portion 48, there can be an increased difficulty with regard to containing the high-absorbency particles within the retention portion and restricting the movement or migration of the superabsorbent onto the bodyside of the diaper. To improve the containment of the high-absorbency material, absorbent structure 32 can include an improved overwrap, such as a wrap sheet 70, placed immediately adjacent and around retention portion 48. The wrap sheet is preferably a layer of absorbent material which covers the major bodyside and outerside surfaces of the retention portion, and preferably encloses substantially all of the peripheral edges of the retention portion to form a substantially complete envelope thereabout. Alternatively, the wrap sheet can provide an absorbent wrap which covers the major bodyside and outerside surfaces of the retention portion, and encloses substantially only the lateral side edges of the retention portion. Accordingly, both the linear and the inwardly curved portions of the lateral side edges of the wrap sheet would be closed about the retention portion. In such an arrangement, however, the end edges of the wrap sheet may not be completely closed around the end edges of the retention portion at the waistband regions of the article.

Absorbent wrap 70 may comprise a multi-element wrapsheet which includes a separate bodyside wrap layer and a separate outerside wrap layer, each of which extends past all or some of the peripheral edges of retention portion 48, as representatively shown in FIG. 1. Such a configuration of the wrap sheet can, for example, facilitate the formation of a substantially complete sealing and closure around the peripheral edges of retention portion 48. In the back waistband portion of the illustrated diaper, the absorbent wrap may also be configured to extend an increased distance away from the periphery of the retention portion to add opacity and strength to the back ear sections of the diaper. In the illustrated embodiment, for example, the bodyside and outerside layers of absorbent wrap 70 extend at least about ½ inch (about 1.3 cm) beyond the peripheral edges of the retention portion to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 70 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs and facilitate the processibility of the absorbent pad.

To provide the bonding between the bodyside and outerside portions of absorbent wrap 70, an adhesive, such as NATIONAL STARCH 72-3723 adhesive, can be printed onto the appointed bonding areas of the absorbent wrap with, for example, a rotogravure-type system. With alternative arrangements having an absorbent wrap composed of a nonwoven meltblown fibrous web, the peripheral sealing of the bodyside and outerside wrap layers may be accomplished by employing hot calendering to provide a sealed strip region around the periphery of the retention portion.

Due to the thinness of retention portion 48 and the high superabsorbent concentrations within the retention portion, the liquid uptake rates of the retention portion, by itself, may be too low, or may not be adequately sustained over multiple insults of liquid into the absorbent structure. The addition of a porous, liquid-permeable layer of surge management material, however, can advantageously improve the overall uptake rate of the composite absorbent structure. Surge management portion 46 is typically less hydrophilic than retention portion 48, and has an operable level of density and basis weight to quickly collect and temporarily hold liquid surges, to transport the liquid from its initial entrance point and to substantially completely release the liquid to other parts of the absorbent structure 32, particularly retention portion 48. This configuration can help prevent the liquid from pooling and collecting on the portion of the absorbent garment positioned against the wearers skin, thereby reducing the feeling of wetness by the wearer.

Various woven and nonwoven fabrics can be used to construct surge management portion 46. For example, the surge management portion may be a layer composed of a meltblown or spunbonded web of polyolefin fibers. The surge management layer may also be a bonded-carded-web or an airlaid web composed of natural and synthetic fibers. The bonded-carded-web may, for example, be a powder-bonded-carded web, an infrared bonded carded web, or a through-air-bonded-carded web. The infrared and through-air bonded carded webs can optionally include a mixture of different fibers, and the fiber lengths within a selected fabric web may be within the range of about 1.0–3.0 inch. The surge management portion may be composed of a substantially hydrophobic material, and the hydrophobic material may optionally be treated with a surfactant or otherwise processed to impart a desired level of wettability and hydrophilicity.

The representative diaper 10 can include a surge management portion 46 which is arranged in a direct, contacting liquid communication with an adjacent absorbent retention portion 48. As representatively shown, surge management portion 46 may be configured for placement adjacent an outwardly facing, outerside of topsheet 28. Optionally, the surge management portion can be placed adjacent an inwardly facing, bodyside surface of topsheet layer 28. The shown configuration of the surge management portion is operably connected to the topsheet layer with a conventional pattern of adhesive, such as a swirl adhesive pattern. In addition, the surge management portion can be operably connected to the bodyside layer of wrapsheet 70 with a conventional pattern of adhesive. The amount of adhesive add-on should be sufficient to provide the desired levels of bonding, but should be low enough to avoid excessively restricting the movement of liquid from the topsheet layer, through the surge management portion and through the wrapsheet layer.

The retention portion 48 is positioned in liquid communication with surge management portion 46 to receive liquids released from the surge management portion, and to hold and store the liquid. In the shown embodiments, surge management portion 46 comprises a separate layer which is positioned over another, separate layer comprising the retention portion, thereby forming a dual-layer arrangement. The surge management portion serves to quickly collect and temporarily hold discharged liquids, to transport such liquids from the point of initial contact and spread the liquid to other parts of the surge management portion, and then to substantially completely release such liquids into the layer or layers comprising retention portion 48.

The representatively shown configuration of the surge management portion is substantially free of absorbent gelling material. Surge management portion 46 may, however, contain a very small amount of particulate gelling material to help acquire an initial liquid surge, but the amount should not be excessive. When excessive amounts of particulate absorbent gelling material are maintained in the target zone, however, the particles can cause the structure to retain and hold unacceptably high amounts of the liquid. In addition, the transport of liquids away from the target zone to other sections of absorbent structure 32, particularly retention portion 48, can be undesirably impaired. As mentioned previously, surge layer 46 can be a separately formed layer, which lies adjacent the outwardly facing surface of topsheet 28 between the retention portion and topsheet. Thus, surge management portion 46 need not comprise the entire thickness of absorbent structure 32. The retention portion can optionally include a recess area which wholly or partially surrounds surge management portion 46, or the retention portion can be entirely positioned below the surge management portion. The arrangement which includes the recess in retention portion 48 can advantageously increase the area of contact and liquid communication between the retention portion and surge management portion 48. It should be understood, however, that surge management portion 46 could optionally be constructed to extend through the entire thickness of absorbent structure 32 so that the capillary flow of liquid into retention portion 48 occurs primarily in a generally sideways (X—Y) direction.

The surge management portion can be of any desired shape consistent with the absorbency requirements of absorbent structure 32. Suitable shapes include for example, circular, rectangular, triangular, trapezoidal, oblong, dog-boned, hourglass-shaped, or oval. Preferred shapes of the surge management portion are those that increase the contacting, liquid communicating surface area between surge management portion 46 and retention portion 48 so that the relative capillarity difference between the portions can be fully utilized. In certain embodiments, for example, the surge management portion can be generally rectangular-shaped.

In the various configurations of the invention, surge management portion 46 may extend over the complete length of retention portion 48, or may extend over only a part of the retention portion length. Where the surge management portion extends only partially along the length of the retention portion, the surge management portion may be selectively positioned anywhere along absorbent structure 32. For example, surge management portion 46 may function more efficiently when it is offset toward the front waistband of the garment and transversely centered within a front section of absorbent structure 32. Thus, surge management portion 46 can be approximately centered about the longitudinal center line of absorbent structure 32, and positioned primarily in a central region of a front section of the absorbent structure 32.

In other aspects of the invention, the end edges of the surge management portion can be spaced longitudinally inboard from the end edges of the retention portion 48. In particular configurations of the invention, the corresponding, relatively adjacent front end edge of surge management portion 46 can be spaced a predetermined discrete distance from a front waistband end edge of the retention portion 48.

It has been found that an effective fabric for constructing the surge management portion can be distinctively characterized by particular parameters. Such parameters include, for example, basis weight, permeability, porosity, surface area per void volume (SA/VV), compression resiliency and saturation capacity. Further parameters can include a bonding matrix which will help stabilize the pore size structure, and hydrophilicity. The bond-matrix and the blend of fiber deniers can advantageously provide for and substantially maintain a desired pore size structure.

Additional details regarding the surge materials and suitable techniques for determining the above-described parameters are set forth in U.S. patent application Ser. No. 206,986 of C. Ellis and D. Bishop, entitled, FIBROUS NONWOVEN WEB SURGE LAYER FOR PERSONAL CARE ABSORBENT ARTICLES AND THE LIKE, and filed Mar. 4, 1994 (attorney docket No. 11,256); and U.S. patent application Ser. No. 206,069 of C. Ellis and R. Everett, entitled, IMPROVED SURGE MANAGEMENT FIBROUS NONWOVEN WEB FOR PERSONAL CARE ABSORBENT ARTICLES AND THE LIKE, and filed Mar. 4, 1994 (Attorney docket No. 11,387); the disclosures of which are hereby incorporated by reference in a manner that is consistent herewith.

In desired configurations of the invention, the surge material can include natural fibers, synthetic fibers, such as synthetic polymer fibers, and combinations thereof. The fabric can, for example, be composed of polyolefin fibers, and in particular configurations the fibers can include bicomponent fibers. For example, polypropylene/polyethylene bicomponent fibers may be employed to form the bicomponent fiber portion of any of the described fabrics. In addition, the bicomponent fibers may be flat crimped or helically crimped.

In the shown configuration of the article, the side panel members 56 are separately provided members which are operably connected and attached to laterally opposed end sections of the back waistband portion of backsheet 30. In particular, each side panel is affixed to extend away from a corresponding terminal edge of the backsheet layer. The side panels can be composed of a substantially non-elastomeric material, such as polymer films, woven fabrics, nonwoven fabrics or the like, as well as combinations thereof. In particular aspects of the invention, the side panels are composed of an elasticized material, such as a stretch-bonded-laminate (SBL) material, a neck-bonded-laminate (NBL) material, an elastomeric film, an elastomeric foam material, or the like. For example, suitable meltblown elastomeric fibrous webs are described in U.S. Pat. No. 4,663,220 issued May 5, 1987 to T. Wisneski et al., the disclosure of which is hereby incorporated by reference. Examples of composite fabrics comprising at least one layer of nonwoven textile fabric secured to a fibrous elastic layer are described in European Patent Application No. EP 0 110 010 published on Apr. 8, 1987 as EP 0 217 032 A2 with the inventors listed as J. Taylor et al., the disclosure of which is hereby incorporated by reference. Examples of NBL materials are described in U.S. Pat. No. 5,226,992 issued Jul. 13, 1993 to M. Mormon, the disclosure of which is hereby incorporated by reference.

Examples of articles which include elasticized side panels and selectively configured fastener tabs are described in U.S. patent application Ser. No. 168,615 of T. Roessler et al., entitled DYNAMIC FITTING DIAPER, and filed Dec. 16, 1993 (Attorney docket No. 10,961). Various techniques for forming the desired fastening systems are described in U.S. Pat. No. 5,399,219 of T. Roessler et al., entitled METHOD FOR MAKING A FASTENING SYSTEM FOR A DYNAMIC FITTING DIAPER and issued Mar. 21, 1995 (Attorney docket No. 11,186); in U.S. patent application Ser. No. 286,086 of D. Fries, entitled A PROCESS FOR ASSEMBLING ELASTICIZED EAR PORTIONS and filed Aug. 3, 1994 (Attorney docket No. 11,169); in U.S. patent application Ser. No. 08/415,383 of D. Fries, entitled AN ASSEMBLY PROCESS FOR A LAMINATED TAPE and filed Apr. 3, 1995 (attorney docket No. 11,950), and in U.S. patent application Ser. No. 08/415,382 of D. Fries, entitled AN ABSORBENT ARTICLE WITH A LAMINATED TAPE and filed Apr. 3, 1995 (attorney docket No. 11,990). The entireties of the disclosures of the above-described documents are incorporated herein by reference in a manner that is consistent (not in conflict) herewith.

The fastener system can include a separately provided reinforcement strip 88 which is composed of a strengthening and/or stiffening material, and is laminated to an appointed first surface of each of the side panel members 56 at the outboard region of the side panel. The shown reinforcement strip extends along substantially the entire length of the outboard end portion of the panel member 56. In addition, the reinforcement strip has a length which is greater than the length dimension of the securing means 44 on the user-bond portion 38 of the fastener tab 36. The reinforcement strip 88 can, for example, be composed of a release tape, and the release tape can include a substrate composed of a polymer film, such as a polypropylene film. Suitable release tape materials are available from Avery Corp., a business having offices located in Painesville, Ohio.

The release tape configuration of the reinforcement strip 88 can have an appointed release surface and an oppositely located attachment surface. A suitable release material, which has a limited low level adhesion to conventional pressure-sensitive adhesives, is positioned and distributed over the release surface, and a suitable attachment mechanism, such as a layer of construction adhesive, is distributed over the attachment surface. The construction adhesive is employed to affix the reinforcement strip 88 onto an appointed section of the final article. In particular, the strip of release tape can be operably bonded and laminated to the outboard region of the panel member 56 along the first surface of the panel member. The shown strip of release tape can be configured with its terminal outboard edge positioned substantially coterminous and substantially coextensive with the outboard edge of the panel member 56. In addition, the width of the release tape along the cross-direction 24 is desirably equal to or greater than the width of the securing means 44 provided on the user-bond region 38 of the fastener tab 36.

The illustrated fastening system includes a complementary, opposed pair of fastener tabs 36, which provide a mechanism for holding the article on the wearer. Each of the fastener tabs includes a tab substrate 86, which may be composed of various substrate materials. For example, the shown embodiment of the tab substrate can be composed of a polymer film, such as a polypropylene film. Suitable film materials are available from Avery Corp., a business having offices located in Painesville, Ohio. Alternatively, the securement web may include a woven or nonwoven fabric, such as spunbond nonwoven fabric.

The representatively shown tab substrate 86 includes an appointed securement surface and an opposed user surface, and includes a selected securing means which is positioned onto the securement surface of the tab substrate. The securing means may be provided by an adhesive, a cohesive material, a cooperating component of a interengaging, mechanical fastener, snaps, pins or buckles and the like, as well as combinations thereof. For example, the securing means may include a hook (e.g. mushroom-head) component or a loop component of a hook-and-loop fastener. In the shown configuration, the securing means is provided by a layer of primary adhesive distributed over the appointed securing surface, and the fastening system provides an adhesive fastener tab. The fastener tabs can be constructed to releasably adhere to an appointed landing zone patch 92 which is attached to the front waistband section of the diaper to provide a refastenable adhesive fastening system.

With the adhesive securing means, the layer of primary adhesive can be employed to operably laminate and affix the appointed factory-bond region 39 of the fastener tab 36 to the outboard region of the panel member 56 along an appointed second surface of the panel member. Other types of connecting means, such as thermal bonds, sonic bonds, mechanical stitching, stapling and the like, as well as combinations thereof, may alternatively be employed to permanently attach the fastener tab to the panel member. For example, ultrasonic bonds may be employed to provide a selected supplemental bonding.

With reference to FIG. 1, the fastener tab 36 includes a factory-bond section 39 which overlaps the outboard edge of the panel member 56, and extends beyond the panel member to provide the user-bond region of the fastener tab. In particular arrangements of the invention, the fastener tab can have a relatively wide user-bond section in combination with a relatively narrower intermediate section. The intermediate section is positioned between the user-bond and factory-bond sections of the fastener tab. In a further aspect of the invention, the fastener tab 36 may optionally include a finger tab region. The finger tab can be substantially non-securing, and can provide an area that can be readily grasped by the user without contaminating or otherwise adversely affecting the securing means.

Various types and arrangements of interengaging mechanical securing means can be employed to provide an operable fastening system for the various configurations of the invention. Representative examples of suitable mechanical fastener configurations are described in U.S. patent application Ser. No. 366,080 by G. Zehner et al., filed Dec. 28, 1994 and entitled HIGH-PEEL TAB FASTENER (attorney docket No. 11,571), and in U.S. patent application Ser. No. 421,640 by P. VanGompel et al., entitled MULTI-ATTACHMENT FASTENING SYSTEM and filed Apr. 13,1995 (attorney docket No. 11,430), the entire disclosures of which are hereby incorporated by reference in a manner that is consistent herewith.

The following Examples are presented to provide a more detailed understanding of the invention. The Examples are intended to be representative, and are not intended to specifically limit the scope of the invention.

EXAMPLES

Example 1

Each sample was composed of a 1.0 mil (0.0254 mm) thick polyurethane film, grade MP 1882 P, available from JPS Elastomerics Corp., a business having offices in Northampton, Mass. The elastomeric film exhibited inadequate, low stiffness values, which were lower than the testing scale of the test instrument.

Example 2

The samples were taken from PAMPERS Stretch diapers which were distributed by the Procter & Gamble Co., a business having offices in Cincinnati, Ohio. The diapers included a waist flap, and test samples of the waist flaps were taken for testing. The size of each waist flap was too small to test as an individual piece of material. As a result, each test sample included the waist flap material attached to connected sections of the diaper liner sheet and the diaper back sheet. The attachment of the added layers of the liner and backsheet materials is believed to have increased the overall stiffness of each test sample. As a result, it is believed that the observed stiffness values were higher than the values that would have been measured if the tests had been conducted on samples composed of the waist flap material alone. The waist flap in each of the samples in this Example 2 was composed of an elastomeric, three-layer laminate. The laminate was composed of one layer of film (polyethylene:polyvinyl acetate copolymer with $TiO_2$ filler) sandwiched between two layers of polypropylene nonwoven, and was thermally bonded together. The samples exhibited stiffness values that were excessively low.

Example 3

The samples were taken from diapers distributed by Molnlycke A.G., a business having offices in Goteborg, Sweden. The diapers included an inner, bodycontacting layer having a relatively large, elongate central opening or aperture therethrough. Longitudinally extending elastics were attached to gather the edge regions of the inner layer which were adjacent the side edges of the aperture. The material of the inner layer located adjacent the longitudinally opposed end edges of the aperture were observed to provide structures which resembled a pair of waist flaps. The Molnlycke diapers provided sufficient material to remove individual samples large enough for stiffness testing. The samples could be taken as if they were removed from raw material stock, and measured 1 inch (2.54 cm) in length by ½ inch (1.27 cm) in width. Each sample was a nonwoven fabric composed of a polypropylene, bonded-carded web. The samples exhibited stiffness values that were excessively low.

Example 4

Each sample was a laminate composed of a 0.00035 inch (about 0.0089 mm) thick polyethylene film, code SF20 available from Consolidated Thermoplastics Co., a business having offices in Chippewa Falls, Wis. The laminate had 12 strands of LYCRA 470 dtex (decitex) elastomer applied stretched at approximately a 260% elongation, with 5 strands within the pocket section 84 and 7 strands within the flange section 82. The film and elastic strands were assembled and attached to a bicomponent polypropylene/polyethylene fiber spunbond web having 0.6 osy (about 20.4 $g/m^2$) basis weight with 6.5 $g/m^2$ of FINDLEY H2096 adhesive employing a meltspray applicator available from J. & M. Laboratories Inc., a business having offices in Dawsonville, Ga. The samples were representative of waist pocket members suitable for the present invention.

Example 5

Each sample was a laminate composed of a 0.00035 inch (about 0.0089 mm) thick polyethylene film, code SF20 available from Consolidated Thermoplastics Co. The laminate had 12 strands of LYCRA 470 dtex elastomer applied at approximately 260% elongation, with 7 strands within the pocket section and with 5 strands within the flange section. The film and elastic strands were glued to a bicomponent polypropylene/polyethylene fiber spunbond fabric having a 0.6 osy (about 20.4 $g/m^2$) basis weight, with 6.5 $g/m^2$ of FINDLEY H2096 adhesive using a meltspray applicator available from J.& M. Laboratories Inc. The samples were representative of waist pocket members suitable for the present invention.

Example 6

Each sample was a laminate composed of a 0.0006 inch (about 0.015 mm) thick polyethylene film, code XEM400.1 available from Consolidated Thermoplastics Co. The laminate had 6 strands of GLOSPAN S7 360 denier, with 2 strands within the pocket section applied at approximately 175% elongation and with 4 strands within the flange section applied at approximately 150% elongation. The film and elastic strands were glued to a bicomponent polypropylene/polyethylene fiber spunbond fabric web having 0.6 osy (about 20.4 $g/m^2$) basis weight with 5 $g/m^2$ of FINDLEY H9214 adhesive using a swirl applicator. The samples were representative of waist pocket members suitable for the present invention.

Example 7

Each sample was a laminate composed of a 0.0006 inch (about 0.015 mm) thick polyethylene film, code XEM400.1 available from Consolidated Thermoplastics Co. The laminate had 6 strands of GLOSPAN S7 360 denier, with 2 strands within the pocket section applied at approximately 175% elongation and with 4 strands within the flange section applied at approximately 150% elongation. The film and elastic strands were glued to a polypropylene spunbond fabric web having 0.6 osy (about 20.4 $g/m^2$) basis weight, with 5 $g/m^2$ of FINDLEY H9214 adhesive using a swirl applicator. The samples were representative of waist pocket members suitable for the present invention.

Example 8

Each sample was a laminate composed of a 0.00035 inch (about 0.0089 mm) thick polypropylene film, code XSF184 available from Consolidated Thermoplastics Co. The laminate had 6 strands of GLOSPAN S7 490 denier, with 2 strands within the pocket section applied at approximately 200% elongation and with 4 strands within the flange section applied at 150% elongation. The film and elastic strands were glued to a bicomponent polypropylene/polyethylene fiber spunbond fibrous web having 0.6 osy (about 20.4 $g/m^2$) basis weight with FINDLEY H2096 adhesive using a strand-coating technique. The samples were representative of waist pocket members suitable for the present invention. The Gurley stiffness values for Examples 1–8 are summarized in the following TABLE 1.

TABLE 1

GURLEY STIFFNESS VALUES
Gurley Stiffness Values (Standard Gurley Units -- milligrams force)

| | | | | Example | | | | |
|---|---|---|---|---|---|---|---|---|
| | 1 | 2 | 3 | 4 | 5 | 6 | 7 | 8 |
| | | | | 12 Strand | 12 Strand | 6 Strand | 6 Strand | 6 Strand |
| | Film | P&G | Molnlycke | 5 Strands in | 7 Strands in | 2 Strands in | 2 Strands in | 2 Strands in |
| Sample | Polyurethane | (waist dam) | (waist dam) | pocket section | pocket section | pocket section | pocket section | pocket section |
| 1 | — | 2.22 | 1.95 | 61.05 | 49.95 | 44.40 | 82.14 | 25.53 |
| 2 | — | 2.78 | 0.83 | 56.61 | 46.62 | 46.62 | 57.72 | 55.50 |
| 3 | — | 3.61 | 0.56 | 75.48 | 48.84 | 57.72 | 55.50 | 26.64 |
| 4 | — | 3.06 | 0.83 | 62.16 | 51.06 | 88.80 | 66.60 | 18.87 |
| 5 | — | 1.95 | 0.83 | 82.14 | 42.18 | 44.40 | 95.46 | 38.85 |
| 6 | — | 2.78 | 0.83 | 83.25 | 58.83 | 77.70 | 117.66 | 39.98 |
| 7 | — | 0.56 | 1.67 | 74.37 | 45.51 | 53.28 | 91.02 | 51.06 |
| 8 | — | 1.95 | 0.56 | 75.48 | 48.84 | 51.06 | 86.58 | 31.08 |
| 9 | — | 3.61 | 1.11 | 63.27 | 51.06 | — | 93.24 | — |
| Ave. | 0.00 | 2.50 | 1.02 | 71.60 | 49.21 | 58.00 | 82.88 | 35.94 |

Ave. = Average
Units of measurement: Standard Gurley Units, which are equivalent to milligrams of force (mf)

During testing, the room was at standard conditions of 73° F. (about 23° C.) and 50% relative humidity. A suitable device for taking the measurements is a Gurley Digital Stiffness tester, Model 4171-D, available from Teledyne Gurley, a business having offices in Troy, N.Y.; or an equivalent device. The testing procedure was in accordance with TAPPI T543 om-94. Examples 1, and 4 through 8 had the Gurley stiffness values obtained from samples taken from raw material supplies of the described films or laminas.

Having described the invention in rather full detail, it will be readily apparent that various changes and modifications can be made without departing from the spirit of the invention. All of such changes and modifications are contemplated as being within the scope of the invention, as defined by the subjoined claims.

We claim:

1. An absorbent article having a longitudinal length dimension, a lateral cross-dimension, a front waistband portion, a back waistband portion, an intermediate portion which interconnects said front and back waistband portions, and having a pair of laterally opposed, elasticized side margins, said article comprising:

a backsheet layer;

a liquid permeable topsheet layer connected in superposed relation to said backsheet layer;

an absorbent body sandwiched between said topsheet layer and said backsheet layer; and an elasticized, separately provided waist pocket member connected along at least one end margin of said article, said waist pocket member including an extending flange section and an extending pocket section;

said flange section assembled and attached to at least one of said backsheet and topsheet layers along said at least one end margin of the article; and said pocket section of said waist pocket member including a substantially fixed edge portion secured to said article, and an elasticized, gathered movable edge portion, said pocket section having a substantially liquid impermeable pocket barrier layer, a pocket fabric layer connected in facing relation with said pocket barrier layer, and a plurality of separate, laterally extending pocket elastic members sandwiched between said pocket barrier layer and said pocket fabric layer to provide an elasticized waist pocket composite which is substantially laterally gathered, wherein said pocket section has a Gurley stiffness value of at least about 5 mg and not more than about 250 mg, as determined about a bending axis aligned substantially parallel to said cross-direction of the article.

2. An article as recited in claim 1, wherein said flange section of said waist pocket member includes a substantially liquid impermeable flange barrier layer;

a flange fabric layer connected in facing relation with said flange barrier layer; and a plurality of separate, laterally extending flange elastic members sandwiched between said flange barrier layer and said flange fabric layer to provide an elasticized flange composite which is substantially laterally gathered by said flange elastic members.

3. An article as recited in claim 2, wherein said pocket section of said waist pocket member is integrally formed with said flange section of said waist pocket member; said pocket barrier layer integrally formed with said flange barrier layer to provide a flange-pocket barrier layer; and said pocket fabric layer integrally formed with said flange fabric layer to provide a flange-pocket fabric layer.

4. An article as recited in claim 3, wherein said flange-pocket barrier layer is substantially coextensive with said flange-pocket fabric layer.

5. An article as recited in claim 3, wherein said elastic members in said flange section are spaced from said elastic members in said pocket section by a boundary space which provides a separation distance of at least about 2 mm.

6. An article as recited in claim 3, wherein at least a one of said elastic members in said pocket section is located between said substantially fixed edge portion and said movable edge portion of said pocket section, and is spaced from said substantially fixed edge portion of said pocket section by a proximal spacing distance of not more than about 20 mm.

7. An article as recited in claim 5, wherein said pocket section of said waist pocket member is secured to said topsheet by a region of attachment which is substantially restricted to said boundary space in at least a section of said boundary space which is in a laterally medial portion of said article.

8. An article as recited in claim 5, wherein said pocket section of said waist pocket member has laterally opposed end sections which are secured to said topsheet to lie substantially flat against said topsheet.

9. An article as recited in claim 5, wherein said pocket section of said waist pocket member is secured to said topsheet with a generally U-shaped arrangement of attachment.

10. An article as recited in claim 5, wherein said backsheet layer includes a terminal waistband edge having an inwardly extending notch region formed therein, and said flange section of said waist pocket member is configured to span across said notch region.

11. An article as recited in claim 2, wherein said flange elastic members are configured to provide a flange contractive force and said pocket elastic members are configured to provide a pocket contractive force, with said flange contractive force greater than said pocket contractive force.

12. An article as recited in claim 1, wherein said pocket elastic members are spaced from a terminal edge of said movable edge portion of the pocket section by a distance of not more than about 13 mm.

13. An article as recited in claim 1, wherein said pocket elastic members are spaced from a terminal edge of said movable edge portion of the pocket section by a distance of not more than about 7 mm.

14. An article as recited in claim 1, wherein a one of said pocket elastic members is located approximately adjacent to and spaced from said terminal edge of said movable edge portion by a distance of not more than about 1 mm.

15. An article as recited in claim 1, wherein said terminal edge is substantially unfolded.

16. An article as recited in claim 1, wherein said pocket section has a Gurley stiffness value of at least about 15 mg, as determined about a bending axis which is aligned along said lateral cross-direction of the article.

17. An article as recited in claim 1, wherein said pocket section has a Gurley stiffness value of at least about 30 mg, as determined about a bending axis which is aligned along said lateral cross-direction of the article.

18. An article as recited in claim 1, wherein said pocket section has a Gurley stiffness value of not more than about 200 mg, as determined about a bending axis which is aligned along said lateral cross-direction of the article.

19. An article as recited in claim 1, wherein said pocket section has a Gurley stiffness value of not more than about 170 mg, as determined about a bending axis which is aligned along said lateral cross-direction of the article.

20. An absorbent article having a longitudinal length dimension, a lateral cross-dimension, a front waistband portion, a back waistband portion, an intermediate portion which interconnects said front and back waistband portions, and having a pair of laterally opposed, elasticized side margins, said article comprising:

a backsheet layer;

a liquid permeable topsheet layer connected in superposed relation to said backsheet layer;

an absorbent body sandwiched between said topsheet layer and said backsheet layer; and an elasticized, separately provided waist pocket member connected along at least one end margin of said article, said waist pocket member including an extending flange section and an extending pocket section;

said flange section assembled and attached to at least one of said backsheet and topsheet layers along said at least one end margin of the article, said flange section having a substantially liquid impermeable flange barrier layer;

a flange fabric layer connected in facing relation with said flange barrier layer; and a plurality of separate, laterally extending flange elastic members sandwiched between said flange barrier layer and said flange fabric layer to provide an elasticized flange composite which is substantially laterally gathered by said flange elastic members;

said pocket section of said waist pocket member including a substantially fixed edge portion secured to said article, and an elasticized, gathered movable edge portion, said pocket section having a substantially liquid impermeable pocket barrier layer, a pocket fabric layer connected in facing relation with said pocket barrier layer, and a plurality of separate, laterally extending pocket elastic members sandwiched between said pocket barrier layer and said pocket fabric layer to provide an elasticized waist pocket composite which is substantially laterally gathered; and wherein said pocket barrier layer is integrally formed with said flange barrier layer to provide a flange-pocket barrier layer, and said pocket fabric layer integrally is formed with said flange fabric layer to provide a flange-pocket fabric layer, said waist pocket member thereby having said flange section integrally formed with said pocket section.

21. An article as recited in claim 20, wherein said flange-pocket barrier layer is substantially coextensive with said flange-pocket fabric layer.

22. An article as recited in claim 20, wherein said pocket section of the waist pocket member has a Gurley stiffness value of at least about 5 mg, as determined about a bending axis which is aligned along said lateral cross-direction of the article.

23. An article as recited in claim 20, wherein said pocket section of the waist pocket member has a Gurley stiffness value of at least about 15 mg, as determined about a bending axis which is aligned along said lateral cross-direction of the article.

24. An article as recited in claim 20, wherein said pocket section of the waist pocket member has a Gurley stiffness value of at least about 30 mg, as determined about a bending axis which is aligned along said lateral cross-direction of the article.

* * * * *